(12) United States Patent
Nesa et al.

(10) Patent No.: US 11,609,226 B2
(45) Date of Patent: Mar. 21, 2023

(54) PORTABLE DEVICE FOR MEASURING THE CONCENTRATION OF AT LEAST ONE COMPONENT IN A GAS EXHALED BY A BREATH FLUID

(71) Applicant: OLYTHE, Aix-en-Provence (FR)

(72) Inventors: Guillaume Nesa, Eguilles (FR); Etienne Flesch, Andresy (FR)

(73) Assignee: OLYTHE, Aix-en-Provence (FR)

( * ) Notice: Subject to any disclaimer, the term of this patent is extended or adjusted under 35 U.S.C. 154(b) by 210 days.

(21) Appl. No.: 17/279,839

(22) PCT Filed: Sep. 30, 2019

(86) PCT No.: PCT/FR2019/052304
§ 371 (c)(1),
(2) Date: Mar. 25, 2021

(87) PCT Pub. No.: WO2020/065241
PCT Pub. Date: Apr. 2, 2020

(65) Prior Publication Data
US 2021/0396735 A1    Dec. 23, 2021

(30) Foreign Application Priority Data

Sep. 28, 2018 (FR) ...................... 1859043

(51) Int. Cl.
*B01L 3/00* (2006.01)
*G01N 35/10* (2006.01)
(Continued)

(52) U.S. Cl.
CPC ........... *G01N 33/4972* (2013.01); *G01N 1/22* (2013.01); *G01N 33/004* (2013.01); *G01N 2001/2244* (2013.01); *G01N 2033/4975* (2013.01)

(58) Field of Classification Search
CPC .... G01N 33/4972; G01N 1/22; G01N 33/004; G01N 2001/2244; G01N 2033/4975
See application file for complete search history.

(56) References Cited

U.S. PATENT DOCUMENTS

| 4,649,027 A | 3/1987 | Talbot |
| 2003/0052692 A1 | 3/2003 | Lin |

(Continued)

FOREIGN PATENT DOCUMENTS

| FR | 2 730 314 B1 | 4/1997 |
| WO | 2011/143693 A1 | 11/2011 |

OTHER PUBLICATIONS

International Search Report dated Feb. 4, 2020 in corresponding International application No. PCT/FR2019/052304; 8 pages.

*Primary Examiner* — Jennifer Wecker
*Assistant Examiner* — Oyeleye Alexander Alabi
(74) *Attorney, Agent, or Firm* — Maier & Maier, PLLC

(57) ABSTRACT

A portable device for measuring the concentration of at least one component in a gas exhaled by a breath fluid, including a first chamber located upstream of a measuring vessel and including an inlet through which the exhaled breath fluid enters the first chamber, a second chamber located upstream of the measuring vessel, the second chamber including an inlet leading into the first chamber, an outlet in communication with the measuring vessel and through which some of the exhaled breath fluid passes, and an outlet leading to the ambient air, through which some of the exhaled breath fluid is expelled into the ambient air. Further, the second chamber is located inside or adjacent the first chamber and the outlet to the ambient air leads to the first chamber so some of the exhaled breath fluid enters the second chamber through the inlet of the second chamber.

28 Claims, 27 Drawing Sheets

(51) Int. Cl.
*G01N 33/497* (2006.01)
*G01N 1/22* (2006.01)
*G01N 33/00* (2006.01)

(56) References Cited

U.S. PATENT DOCUMENTS

2013/0102018 A1* 4/2013 Schentag ............... G01N 21/05
  435/25
2016/0338620 A1 11/2016 Masavage
2017/0100057 A1 4/2017 Wang

* cited by examiner

PORTABLE DEVICE FOR MEASURING THE CONCENTRATION OF AT LEAST ONE COMPONENT IN A GAS EXHALED BY A BREATH FLUID

TECHNICAL FIELD

The invention relates to a portable device for measuring the concentration of at least one component in a gas exhaled by a breath fluid. The invention also relates to a method for operating and a method for using such a device.

The invention relates to the technical field of portable electronic devices such as, for example, breathalyzers or breath testers, in order to measure or detect the concentration of a component of a gas exhaled by a breath fluid.

BACKGROUND

Document FR2730314B1 (SERES) discloses a portable device for measuring the concentration of at least one component in a gas exhaled by a breath fluid, comprising:
 a mouthpiece through which the breath fluid is exhaled,
 a housing incorporating:
  a measuring vessel,
  a measurement means for measuring the concentration of at least one component in a gas of the breath fluid flowing in the measuring vessel,
  an opening into which the mouthpiece is installed.
The mouthpiece comprises:
 a first chamber comprising an inlet through which the exhaled breath fluid enters said first chamber,
 a second chamber adjacent to the first chamber, said second chamber comprising:
  an inlet leading into the first chamber,
  a first outlet in fluid communication with the measuring vessel and through which a portion of the exhaled breath fluid passes,
  a second outlet leading to the ambient air, through which the portion of the breath fluid that is not flowing in the measuring vessel is expelled into the ambient air.

The inlet of the first chamber and the second outlet to the ambient air of the second chamber are aligned along the same axis and have substantially the same cross-section. In the event of strong blowing pressures, the expulsion of air to the ambient air through the second outlet creates negative pressures at the first outlet of the second chamber due to the Venturi effect. This results in a local suction of the air present in the measuring vessel. Measuring the concentration of a component of interest in the exhaled breath fluid is therefore greatly affected and may not be representative of the actual quantity of the component of interest in said fluid.

In order to remedy this problem, the solution implemented in most of the portable measurement devices known from the prior art consists in using a pumping means capable of creating a large partial vacuum at the measuring vessel outlet so as to offset this Venturi effect. Apart from the cost of such a component, this solution is challenging when attempting to further miniaturize said devices and reduce the size of the batteries used. Indeed, such a pumping means is a non-negligible source of energy consumption and is relatively bulky.

The invention aims to remedy these problems. In particular, one purpose of the invention is to ensure the measurement reliability and accuracy of the measurement device while simplifying its design and reducing its manufacturing cost.

Another objective of the invention is to propose a measurement device with a design making it particularly compact compared to the known devices of the prior art.

A device is also known from patent document US2017/0100057 (WANG) in which the enclosure has a housing leading to an opening into which the mouthpiece is inserted.

In this type of device, the installation of electronic components (e.g. measurement means, pumping means, control unit) in the enclosure is generally costly in terms of time and labor. Indeed, the enclosure may be of such a reduced size that the installation of the components and the securing and connection thereof is difficult.

In addition, when one of the electronic components fails, the replacement and/or repair thereof become problematic. Indeed, this requires disassembly of the enclosure, testing of the components to diagnose the failure, completion of the repair, closing of the enclosure, and possibly recalibration of the device. The completion of all these steps can be tedious and time-consuming. In addition, it requires total neutralization of the device, that is, the device cannot be used.

Given this state of affairs, a subsidiary objective of the invention is to reduce the assembly time of various electronic components of the device and to facilitate the installation of these electronic components in the enclosure.

Another subsidiary objective of the invention is to propose a device with a design allowing a defective electronic component to be serviced, while reducing the down time of the device.

SUMMARY

The solution proposed by the invention is a portable device for measuring the concentration of at least one component in a gas exhaled by a breath fluid, of the type described in the aforementioned patent document FR2730314B1. The device is remarkable in that:
 the second chamber is located inside the first chamber or in a position adjacent to said first chamber,
 the outlet to the ambient air leads to the first chamber in such a way that only a portion of the exhaled breath fluid flowing in said first chamber enters the second chamber through the inlet of said second chamber, the other portion of the exhaled breath fluid being expelled into the ambient air.

By means of this design, expulsion of the portion of the breath fluid into the ambient air now takes place in the first chamber and not in the second chamber. This prevents a partial vacuum from occurring due to the Venturi effect at the outlet of the second chamber communicating with the measuring vessel. There is no local suction of the air present in this chamber and, accordingly, the measurements are reliable and accurate. Furthermore, there is no need to provide a pumping means to create a partial vacuum at the outlet of the measuring vessel. Without this component, the overall size of the device can be reduced and the electrical power consumption decreased.

Other advantageous features of the invention are listed below. Each of these features may be considered individually or in combination with the remarkable features defined above, and may form the subject matter of one or more divisional patent applications:
 According to one embodiment, the first chamber and the second chamber are made in the mouthpiece.
 According to an embodiment variant, the first chamber and the second chamber are made in the enclosure.
 According to another embodiment variant, the measuring vessel, the measurement means, a pumping means for extracting the breath fluid flowing in the measuring vessel, and the control unit are grouped together on a common substrate so as to form a grippable unitary assembly, said assembly being removably installed in the housing of the enclosure; the first chamber and the second chamber are made in the common substrate.

According to one embodiment, the second chamber is of a reduced size compared to the size of the first chamber.

According to one embodiment, the measuring vessel, the measurement means, a pumping means, and the control unit are grouped together on a common substrate so as to form a grippable unitary assembly, said assembly being removably installed in the housing of the enclosure.

According to one embodiment, the enclosure is made of at least two elongated tubes having the same longitudinal axis, said tubes fitting together along said longitudinal axis in order to define the housing; the unitary assembly is installed in one of the tubes, said tube forming a mouthpiece holder into which the mouthpiece is inserted.

According to one embodiment, the other tube forming the enclosure is for receiving an electric battery pack for providing power to the grippable unitary assembly.

According to one embodiment, the common substrate is for providing fluid communication between the measuring vessel and the outlet of the second chamber.

According to one embodiment, the common substrate comprises: —a housing in which the measuring vessel is installed; —at least one housing in which the measurement means is installed; —one housing in which the pumping means is installed; —one or more features for receiving the control unit.

According to one embodiment, the common substrate comprises: —a first drill hole leading into a housing in which the measuring vessel is installed, so that said drill hole is in fluid communication with said chamber; —a second drill hole leading into a chamber made in said substrate and in which a pressure sensor is installed; —the outlet of the second chamber is in fluid communication with the first drill hole and the second drill hole.

According to one embodiment, the first drill hole is conical and comprises a first hole and a second hole that leads into the housing in which the measuring vessel is installed, the diameter of said first hole being less than the diameter of said second hole.

According to one embodiment, the outlet to the ambient air is sized so that 80% to 98% of the breath fluid exhaled into the first chamber is expelled into the ambient air.

According to one embodiment: —the inlet of the first chamber, the inlet of the second chamber, and the outlet of said second chamber are arranged in the same alignment; —the outlet to the ambient air is oriented in a direction perpendicular to this alignment.

According to one embodiment, the housing in which is the pumping means is installed comprises a drill hole leading into the housing in which the measuring vessel is installed, so that said housings are in fluid communication with each other.

According to one embodiment: —the measuring vessel and the enclosure each have a longitudinal axis and these longitudinal axes are parallel; —a pumping means is configured to expel the breath fluid flowing in the measuring vessel in a direction parallel to said longitudinal axes.

According to one embodiment: —the measuring vessel is made from a pliable, flexible substrate made in the shape of a tube; —one side of the pliable, flexible substrate is covered with a reflective metal material forming an optical reflection layer; —the pliable, flexible substrate incorporates a resistive heating element; —the pliable, flexible substrate comprises two opposing longitudinal edges that are secured to each other by bonding so as to maintain the shape of said substrate in the form of a tube; —one of said edges has a strip free of any resistive heating element.

According to one embodiment: —the measuring vessel is made from a pliable, flexible substrate made in the shape of a tube; —the pliable, flexible substrate comprises a first side and a second side, and said sides are opposed; —the first side is covered with a reflective metal material forming an optical reflection layer; —the pliable, flexible substrate incorporates a resistive heating element and said heating element is in the form of a flexible electrical circuit into which are integrated one or more heating filaments in the form of strips of metal 1 µm to 50 µm thick arranged on the second side.

According to one embodiment, the heating filament or filaments cover the pliable, flexible substrate homogeneously in such a way that the density of electrical power generated by the resistive heating element is identical over the entire second side of said substrate.

According to an embodiment variant, the heating filament or filaments cover the pliable, flexible substrate non-homogeneously in such a way that the density of electrical power generated by the resistive heating element varies along a longitudinal axis and/or along a transverse axis of the pliable, flexible substrate.

According to one embodiment, the heating filaments form resistive heating sub-assemblies that are connected electrically in parallel.

According to one embodiment: —the measuring vessel is in the form of a tube open at both ends; —the measurement means comprises an infrared radiation emitter installed at one end of the measuring vessel so that an infrared radiation passes through said chamber, and an infrared radiation detector installed at the other end of the measuring vessel; —a cavity sealed against the breath fluid is placed between the infrared radiation emitter and the corresponding end of the measuring vessel; —a cavity sealed against the breath fluid is placed between the infrared radiation detector and the corresponding end of the measuring vessel.

According to one embodiment, said device is a breathalyzer or a breath tester.

Another aspect of the invention refers to a method for regulating the temperature of the measuring vessel of the device, consisting in regulating the electrical energy injected into the resistive heating element thanks to a negative feedback loop based on: real-time measurement of the resistance of said element and the objective of achieving a resistance setting corresponding to a target heating temperature.

Another aspect of the invention refers to a method of using the device comprising steps consisting in:
  recording and associating a means of identification of the device and a means of identification of a user in a database,
  prior to measurement, acquiring the means of identification of the device and the means of identification of the user from a mobile terminal of the user, analyzing the acquired means of identification of the device and the acquired means of identification of the user, sending an instruction to the control unit to take the measurement only in the event of a match between the acquired means of identification of the device and the acquired means of identification of the user, said instruction being generated from the mobile terminal.

Acquisition of the user's means of identification is based advantageously on the implementation of an algorithm for facial recognition of said user.

Acquisition of the means of identification of the device may be based on the implementation of an algorithm for recognizing the shape of said device or on the implementation of an algorithm for recognizing a marking placed on said device.

BRIEF DESCRIPTION OF THE FIGURES

Other advantages and features of the invention will become clear from a reading of the following description of a preferred embodiment, in reference to the appended drawings, given as non-limiting examples, in which:

FIG. 1b is a rear perspective view of the device in FIG. 1a,

DETAILED DESCRIPTION OF THE EMBODIMENTS

The device of the invention is intended to measure the concentration of at least one component (ethanol and/or acetone and/or CO and/or $CO_2$ and/or $H_2O$ and/or etc.) in a gas exhaled by a breath fluid. It is particularly well suited, but not exclusively, for use as a breathalyzer or breath tester to detect and/or check blood alcohol levels, such as before driving a vehicle. It can also be used by diabetics to indirectly check their blood sugar level by measuring the concentration of acetone in their breath fluid. In the remainder of the description, the expressions "gas exhaled by a breath fluid," "breath fluid," or "gas of the/of breath fluid" are synonymous.

The device is portable in that it is self-contained and sufficiently small to be placed in a clothing pocket, for instance.

Figure 1A:
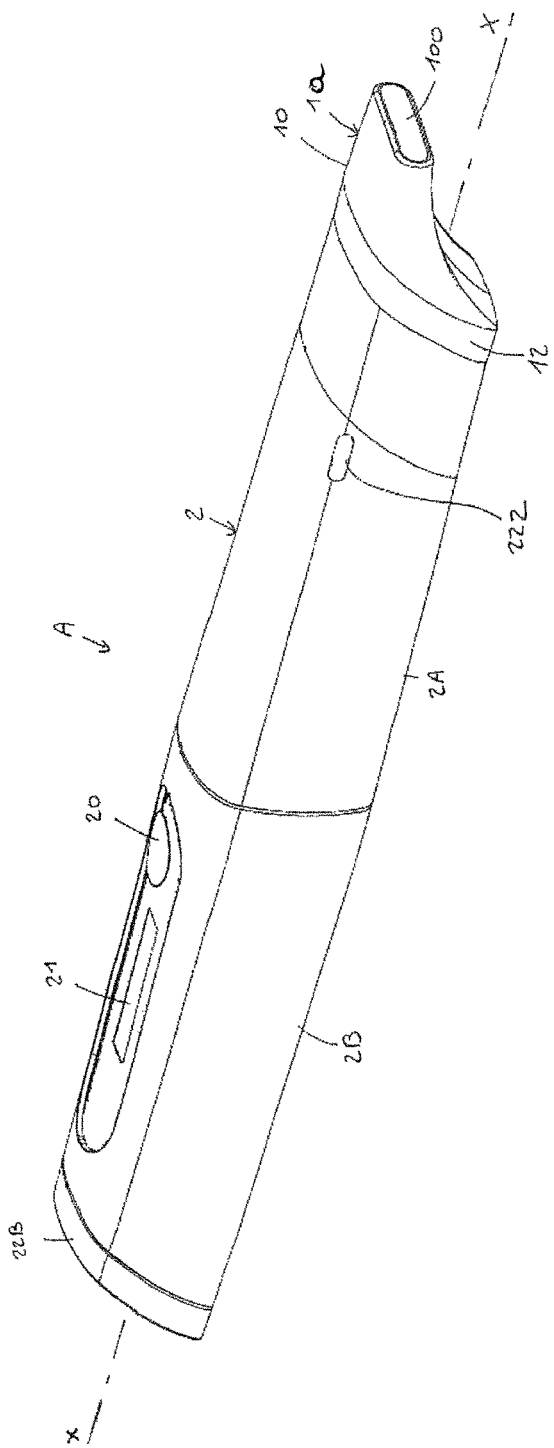
FIG. 1a is a front perspective view of a device according to the invention.
Figure 1B:
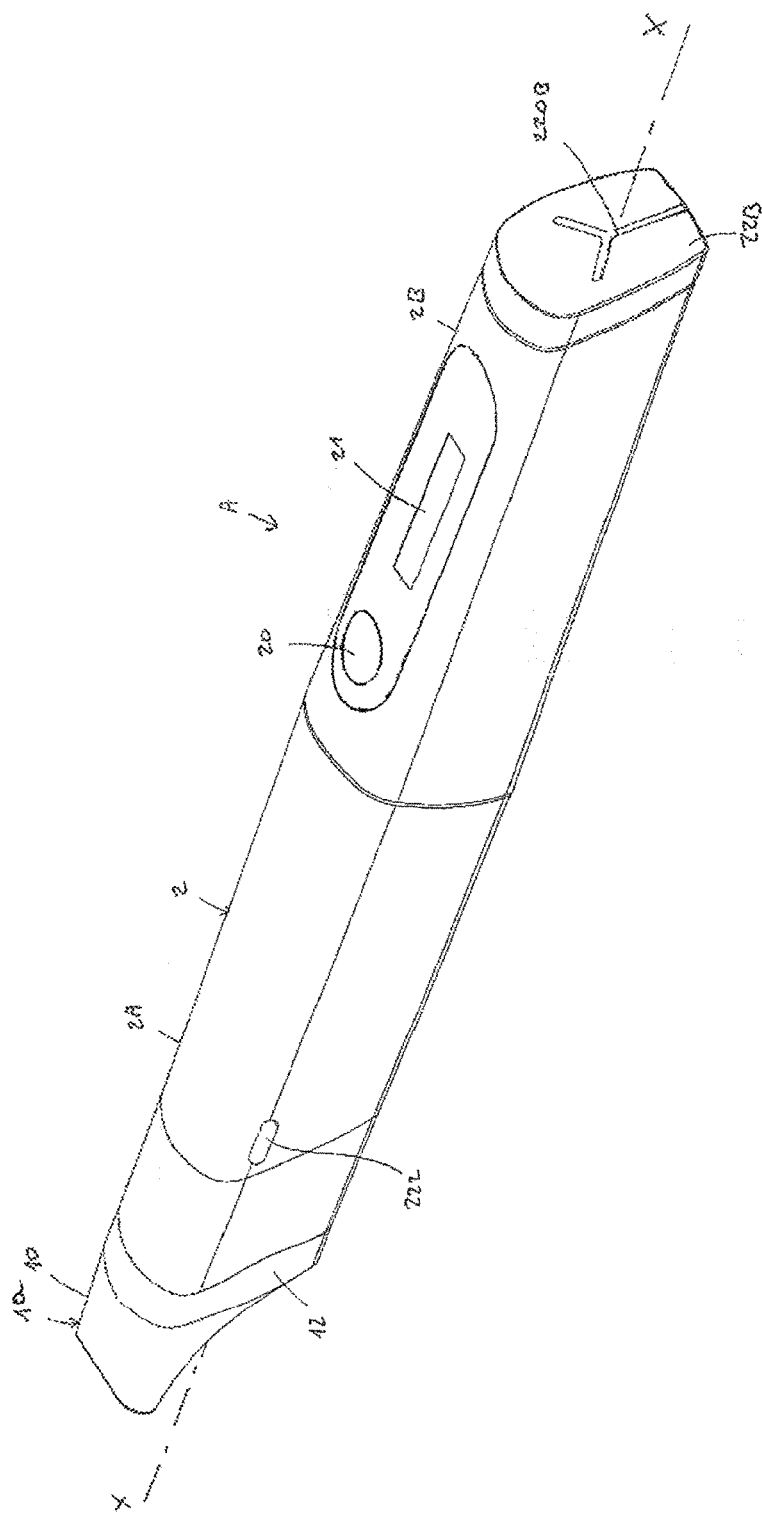

In FIGS. 1a and 1b, device A has an elongated shape and has a longitudinal axis X-X. It lies advantageously within a parallelepiped envelope having a length of between 10 cm and 15 cm, a width of between 1 cm and 3 cm, and a height of between 1 cm and 3 cm. Device A can therefore be considered compact, with a particularly small overall size.

Device A comprises a mouthpiece 1 through which the breath fluid exhaled by the user passes. In the appended figures, mouthpiece 1 has the shape of a recorder mouthpiece. It is assembled to one end of an enclosure 2.

Mouthpiece 1 and enclosure 2 are made of a rigid material, such as synthetic or biobased plastic (e.g. PVC, ABS, PC, PA, PLA, PHA, PHB, PBS), carbon, composite material, steel, and so on. They can be obtained by molding, extrusion, printing, or by any other method suitable for a person skilled in the art. They do not require any special surface treatment.

In FIGS. 1a and 1b, enclosure 2 comprises an accessible pressable button on the wall thereof for turning device A on and off, and a means of information 21 for displaying the concentration value of the component or components of the measured gas. This means of information 21 is preferably an OLED display screen. Means of information 21 could also consist of a loud speaker using sound to indicate the measured value, and/or one or more indicator lights having a color depending on the measured value.

Figure 2A:
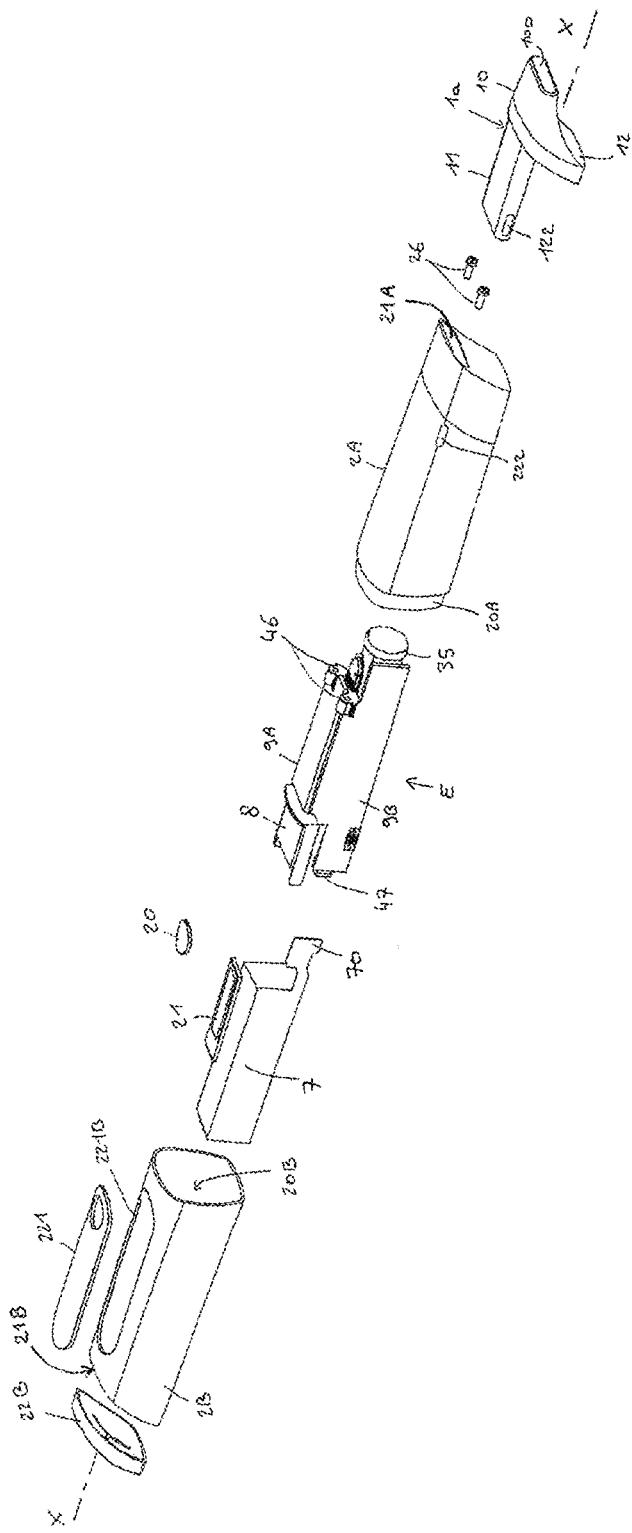
FIG. 2a is a front exploded perspective view of the device in FIGS. 1a and 1b.
Figure 2B:
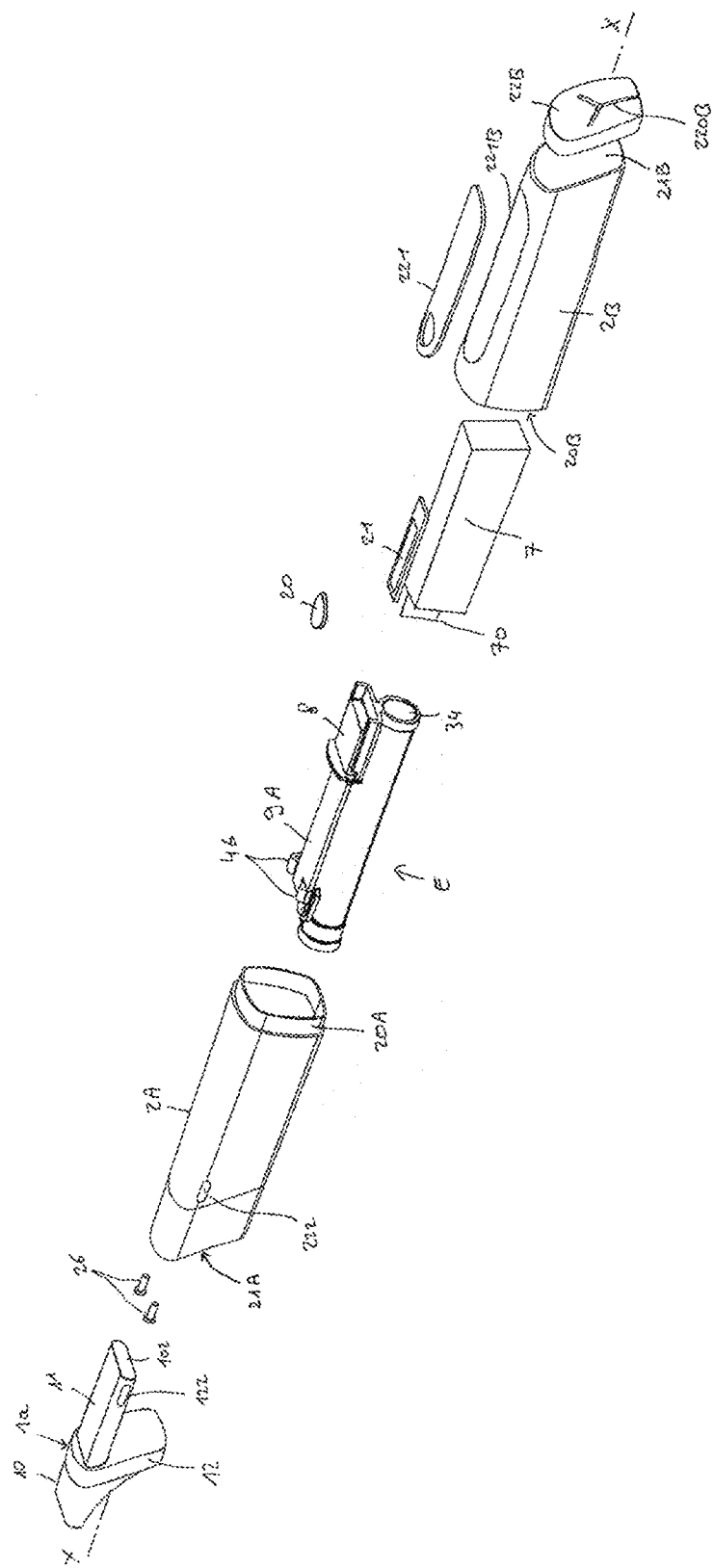
FIG. 2b is a rear exploded perspective view of the device in FIGS. 1a and 1b.

Enclosure 2 has a housing in which the various components of device A are installed. In FIGS. 2a and 2b, enclosure 2 is made of two elongated tubes 2A, 2B having axis X-X as a common longitudinal axis. These two tubes 2A, 2B fit together along longitudinal axis X-X. This particularly simple design has several advantages: it makes it possible to build enclosure 2 with simple shapes, thereby reducing manufacturing costs. In addition, assembly of enclosure 2 is done very quickly. And lastly, assembly/disassembly of the various components inside enclosure 2 can also be done very quickly.

Tubes 2A, 2B are hollow such that their inside wall delimits the housing of enclosure 2. Said tubes made have a circular, square, rectangular, or other cross-section. Front tube 2A has an open end 20A of which the inside wall is shaped to form a male connection member. And rear tube 2B has a complementary open end 20B of which the inside wall is shaped to form a female connection member to removably receive the male connection member of front tube 2A. One or more latching parts may be provided to hold the two tubes 2A, 2B effectively in position. A solution with screws or bonding (for example, with an adhesive) of tubes 2A, 2B may also be considered. As explained further in the description, the two tubes 2A, 2B delimit a housing in which the various components of device A are installed. The other open end 21B of rear tube 2B is closed off with a cap 22B, which comprises an opening 220B establishing fluid communication between the inside of said tube and the ambient air.

In reference to FIG. 2a, front tube 2A has an opening 21A into which mouthpiece 1a is inserted. As such, front tube 2A serves as a mouthpiece holder. It should be noted that the housing of enclosure 2 leads to this opening 21A. For the sake of good hygiene, mouthpiece 1a is advantageously disposable such that it can be disconnected from enclosure 2 and more specifically opening 21A. The fact that mouthpiece 1a is disposable requires that the shape thereof be as simple as possible and that it be of minimal weight to keep the cost of the manufacturing process and of the materials of these mouthpieces as low as possible. Certain special uses of the measurement device for medical applications or for intensive use may require the use of biocompatible or biodegradable materials for environmental or regulatory reasons. Consequently, all of these requirements can be taken into account in the design of such mouthpieces.

Figure 7:
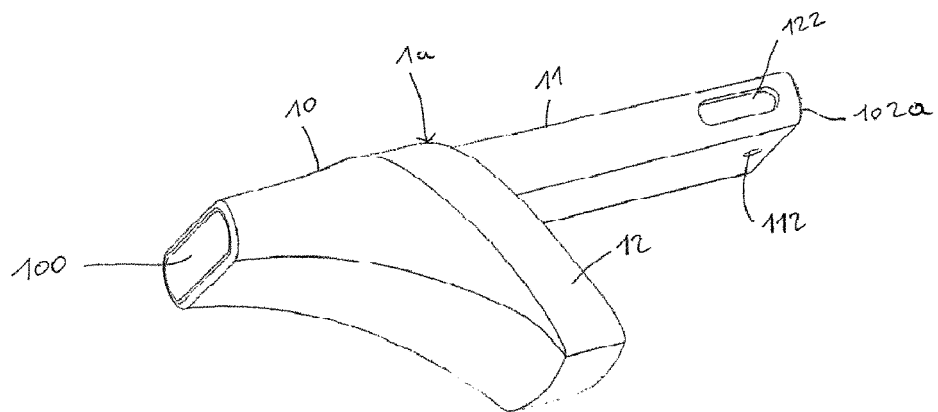
FIG. 7 is a perspective view of a mouthpiece for cooperating with the common substrate of FIGS. 4 to 6.

In FIGS. 2a, 2b, and 7, mouthpiece 1a has a tip 10 with an inlet 100 through which the breath fluid is exhaled. In practice, the user places the lips on tip 10 and exhales through inlet 100. Inlet 100 has an oblong shape, the width of which is substantially equal to that of device A. The height of inlet 100, for example, is between 1 mm and 10 mm. Tip 10 is extended along axis X-X with a core 11, the cross-section of which is substantially equal to that of inlet 100. This core 11 is what engages with opening 21A of front tube 2A. For example, core 11 is 10 mm to 30 mm long. Mouthpiece 1a also has a skirt 12 arranged at the interface between tip 10 and core 11, said skirt covering the end of front tube 2A having opening 21A. This skirt 12 also serves as a gripping means for removing mouthpiece 1a without touching the portion of tip 10 that has come into contact with the user's lips.

In accordance with the invention, two chambers are placed upstream of a measuring vessel 3 installed in enclosure 2.

First Embodiment

According to a first embodiment, the two chambers are made in mouthpiece 1a.

Figure 8:
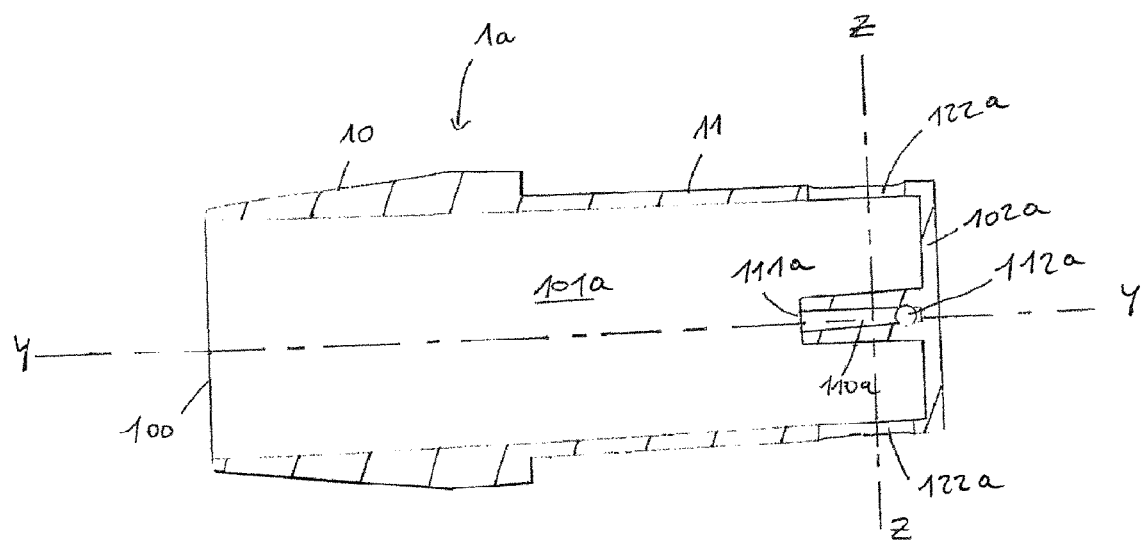
FIG. 8 is a longitudinal cross-sectional view of the mouthpiece in FIG. 7.

In FIG. 8, tip 10 and core 11 delimit a first chamber 101a to which inlet 100 leads. The exhaled breath fluid therefore flows into first chamber 101a. A bottom wall 102a, located at the opposite end of inlet 100, closes off first chamber 101a.

A second chamber 110a is placed inside first chamber 101a. This second chamber 110a is preferably of a small size compared to the size of first chamber 101a. While the length of first chamber 101a corresponds to the combined length of tip 10 and core 11, the length of second chamber 110a is only a fraction (e.g. ⅐) of that length. The same is true of the width of second chamber 110a, which is only a fraction (e.g. ⅓) of the width of first chamber 101a.

Second chamber 110a comprises an inlet 111a which leads to first chamber 101a and through which a portion of the exhaled breath fluid flowing in said first chamber passes. Inlet 111a has the same cross-section, or substantially the same cross-section, as that of second chamber 110a. Bottom wall 102a, located at the opposite end of inlet 111a, also closes off second chamber 110a. The portion of the exhaled breath fluid flowing in second chamber 110a is extracted from mouthpiece 1a via an outlet 112a. This outlet 112a is in fluid communication with measuring vessel 3 as explained later in the description. Outlet 112a may have a circular cross-section and a diameter corresponding substantially to the width of second chamber 110a. The surface area of outlet 112a is less than the surface area of inlet 100.

Holes 100, 111a, and 112a are arranged in the same Y-Y alignment. This alignment is parallel to the aforementioned longitudinal axis X-X. This linear configuration allows the breath fluid blown into mouthpiece 1a to follow a direct path between inlet 100 and outlet 112a, thereby limiting pressure losses. In addition, the distance separating inlet 100 from outlet 112a can be relatively short, in particular less than 50 mm, so that mouthpiece 1a is particularly compact.

The other portion of the exhaled breath fluid that is not flowing in second chamber 110a is expelled to the ambient air by at least one outlet 122a leading into first chamber 101a. Preferably, two outlets 122a made in the wall of core 11 near bottom wall 102a, are provided. These outlets 122a are lateral holes, that is, they are oriented along a direction Z-Z perpendicular to the alignment Y-Y of holes 100, 111a, and 112a. This particular configuration of mouthpiece 1a affords greater comfort for the user compared to the known mouthpieces of the prior art, in which the inlet of the exhaled breath fluid and the outlet (allowing the portion of fluid not needed for the concentration measurement to be expelled to the ambient air) are aligned along the same axis. Indeed, when a person is located in front of the user, the portion of the exhaled breath fluid that is expelled into the ambient air does not reach the person directly, but instead escapes laterally so that said person does not have to breathe it.

Figure 9:
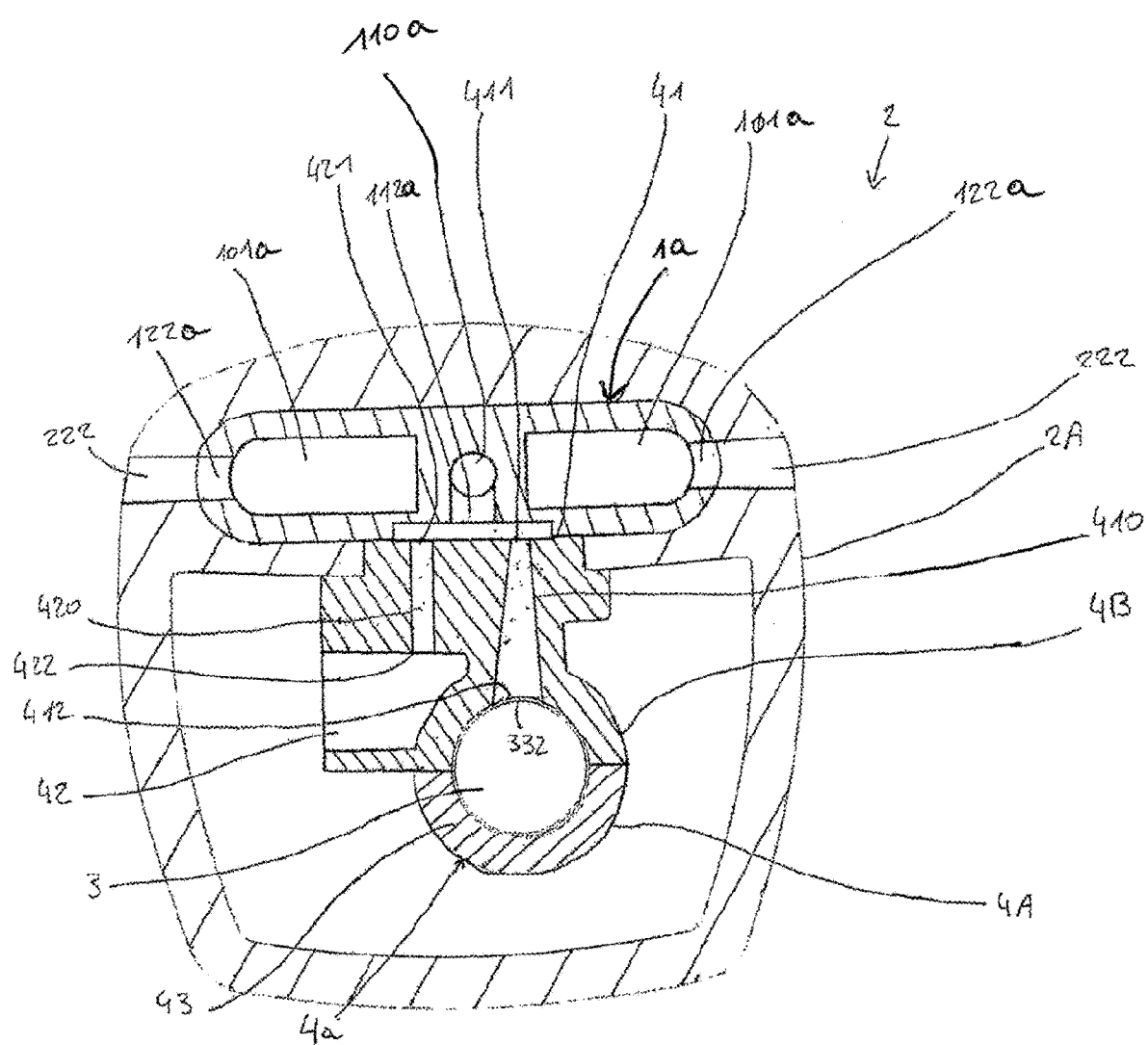
FIG. 9 is a transverse cross-sectional view of the mouthpiece in FIGS. 7 and 8 and of the common substrate in FIGS. 4 to 6, installed in the enclosure.

In reference to FIG. 9, when mouthpiece 1a is installed in opening 21A, outlets 122a are opposite holes 222 arranged laterally on enclosure 2, and more specifically on front tube 2A. These lateral holes 222 can also be seen in FIGS. 1a, 1b, 2a, and 2b.

As shown in FIG. 8, inlet 111a of second chamber 110a is advantageously located upstream of outlets 122a. And the lateral walls of second chamber 110a preferably have dimensions along axis Y-Y that are greater than the dimensions of outlets 122a. Thanks to the position of inlet 111a and/or the length of the lateral walls of second chamber 110a, the turbulence of the exhaled fluid generated in first chamber 101a at outlets 122a does not disrupt the sampling of the breath gas in said second chamber and consequently in chamber 3. The flow of the sampled breath fluid is generally laminar starting with inlet 111a of second chamber 110a.

The combined surface area of outlets 122a is advantageously less than the surface area of inlet 100 of first chamber 101a and greater than the surface area of outlet 112a of second chamber 110a, such that only a small fraction of the breath fluid passing through inlet 100 comes out of outlet 112a, most of said fluid being expelled into the ambient air through outlets 122a.

Through the design of mouthpiece 1a and the configuration of the various holes thereof, when the user blows through inlet 100 of first chamber 101a, the exhaled breath fluid is pressurized in said first chamber. A portion of the breath fluid enters second chamber 110a and comes out through outlet 112a. This sample of the breath fluid coming out of outlet 112a then enters measuring vessel 3 under pressure. Outlets 122a, 222 create an escape that reduces the blowing pressure required for proper operation of device A.

In order to measure the concentration of a component in the breath fluid gas, enclosure 2 includes: a measuring vessel 3 into which the sample of breath fluid coming from mouthpiece 1a through outlet 112a flows; a means of measurement 34, 35; possibly a pumping means 8 for extracting the breath fluid flowing into the measuring vessel; a control unit 9 to control and monitor at least measurement means 34, 35, and, if applicable, pumping means 8 and means of information 21. The concentration measurement is based on the Beer-Lambert law, which is well known to a person skilled in the art.

In FIGS. 5, 18a, 18b, 18c, and 18d, measuring vessel 3 is made of a pliable, flexible substrate 30 in the form of a tube.

Substrate 30 preferably consists of a thin film having a thickness of between 1 μm and 250 μm, preferably about 25 μm. A good flexibility-to-strength ratio is obtained with these thickness values. Substrate 30 is advantageously made of a material chosen from the following group: polyimide (for example: Kapton®), polyepoxide, polyester, fiberglass-reinforced epoxy resin, aluminum substrate (for example: COOL-CLAD® substrate marketed by AI TECHNOLOGY). However, any other material generally used in the manufacture of flexible printed circuits may be considered. Substrate 30 can be obtained by molding, extrusion, lamination, and so on.

Substrate 30 comprises two sides 30a, 30b which are opposite each other. One of sides 30a of substrate 30 is covered with a reflective metal material forming an optical reflection layer off of which an emitted infrared radiation will reflect. This reflection thus guides the emitted infrared radiation. In order for the reflection layer to be as reflective as possible and to limit the energy losses of the emitted radiation, the reflective metal material is preferably chosen from the following group: gold, cobalt, silver, nickel, copper, aluminum, chromium, and zinc. This reflective metal material has a thickness of between 0.01 μm and 500 μm, preferably between 0.01 μm and 10 μm. It may be deposited bonding, electrochemical deposition, electrolytic deposition, printing, silk screening, heating, or by any other method of thin-layer deposition. In order to ensure that the reflective metal material is properly held in position on side 30a of substrate 30, one or more bonding layers may be deposited on that side. These consist, for instance, of layers of materials such as copper, aluminum, silver, nickel, palladium, polyethylene, or a combination of these materials, the total thickness of which is typically between 0.1 μm and 500 μm, preferably between 0.1 μm and 200 μm, deposited by a method of thin-layer deposition. The bonding layer is not indispensable and may be avoided if, for instance, the reflective metal material is deposited by electrolytic deposition.

A flexible resistive heating element 33 is deposited on at least one of sides 30a and/or 30b of substrate 10. In FIG. 10a, heating element 33 is placed on side 30b opposite side 30a covered with the reflective metal material. Heating element 33 may consist of a thin heating resistor secured to substrate 30, such as by bonding, lamination, electrochemical deposition, electrolytic deposition, printing, silk screening, vacuum deposition, heating, mechanical attachment, or by any other method of thin-layer bonding.

Figure 18A:
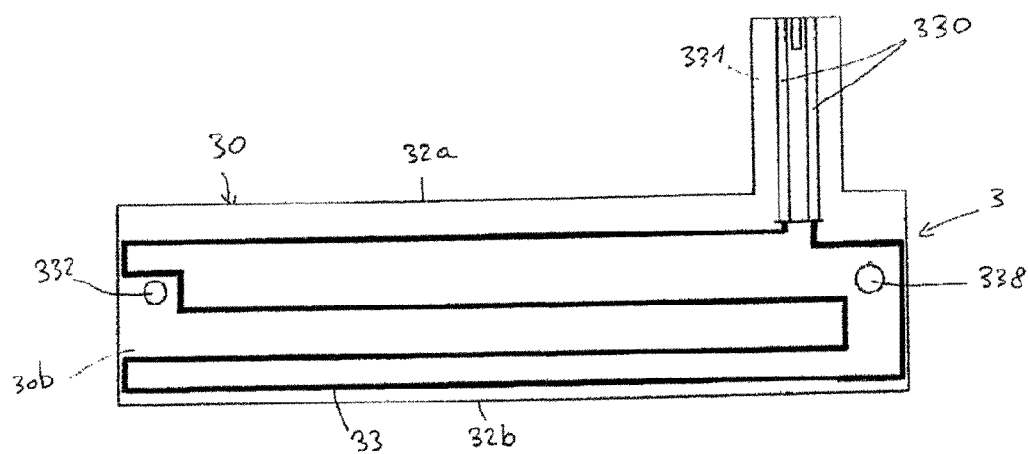
FIG. 18a is a front view of a variant of a pliable, flexible substrate forming the measuring vessel, with said substrate being flat.

According to an advantageous feature of the invention, heating element 33 is in the form of a flexible electric circuit into which one or more heating filaments are integrated. For example, these heating filaments are in the form of strips of metal (copper, copper-nickel, aluminum, etc.) 1 μm to 50 μm thick, arranged on side 30b of substrate 30. These heating filaments can cover pliable, flexible substrate 30 homogeneously as shown in FIG. 18a, so that the electrical power density generated by resistive heating element 33 is identical over entire side 30b of said substrate.

Figure 18B:
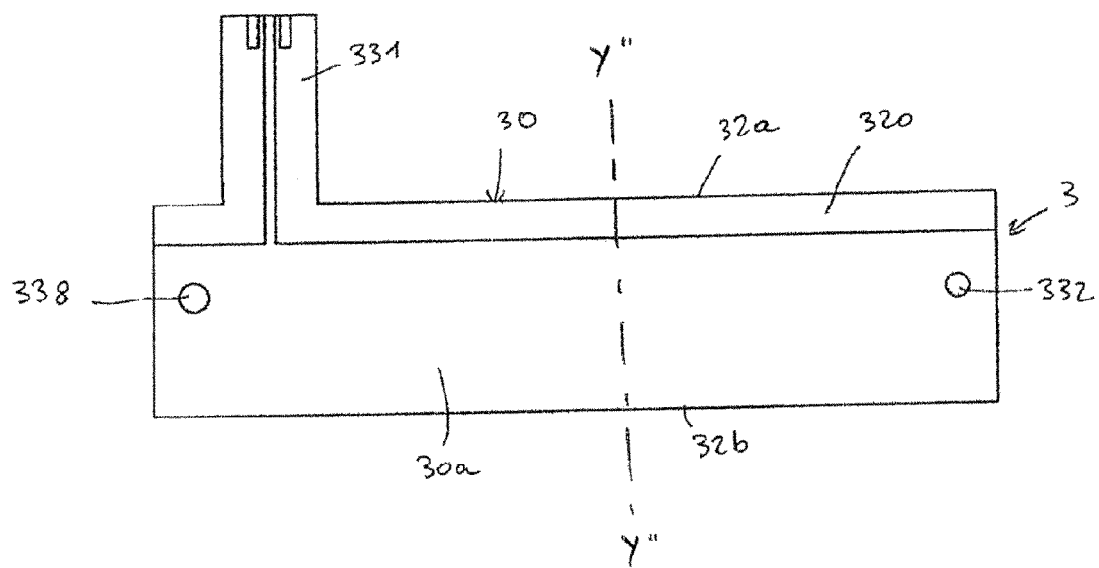
FIG. 18b is a view of the other side of the substrate in FIGS. 18a, 18c, and 18d.
Figure 18C:
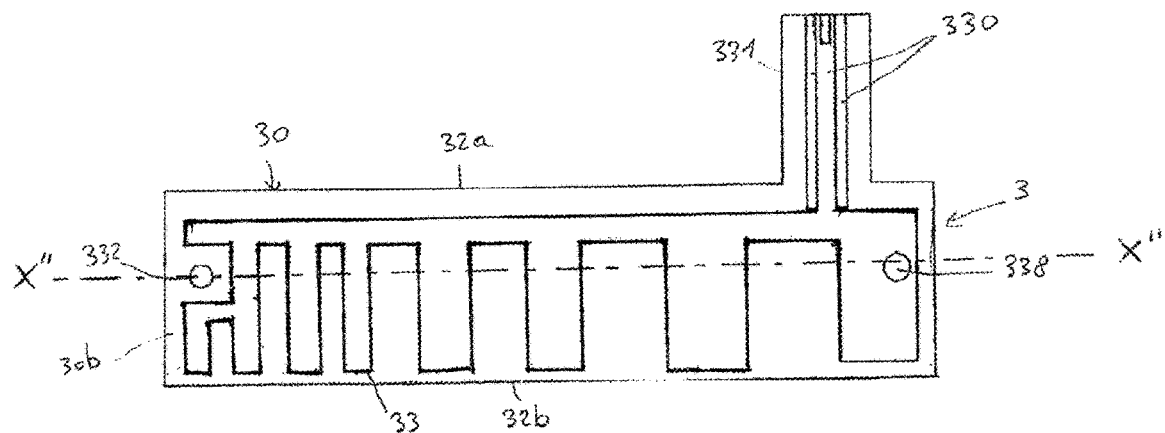
FIG. 18c is a front view of a variant of a pliable, flexible substrate forming the measuring vessel, with said substrate being flat.

In an embodiment variant shown in FIG. 18c, the heating filaments cover substrate 30 non-homogeneously. The surface density of heating filaments may vary according to longitudinal axis X"-X" of flexible substrate 30 so that the inlet of measuring vessel 3 containing hole 332 through which the exhaled breath fluid enters may be heated more. This variation may be even or not (for example, there are three areas of different densities in FIG. 18c). Consequently, the surface density of heating filaments along longitudinal axis X"-X" is greater on side 30b containing hole 332 than on the opposite side containing hole 338. Indeed, the thermal perturbations in dynamics induced by the circulation of breath fluid when a user blows into mouthpiece 1a tend toward greater cooling of inlet 332 of chamber 3 compared to outlet 338 of said chamber. Such an arrangement of resistive heating element 33 makes it possible to compensate for these temperature gradients inherent in the sampling of exhaled breath fluid, and to make the temperature of chamber 3 as homogeneous as possible in order to achieve greater measurement accuracy.

Figure 18D:
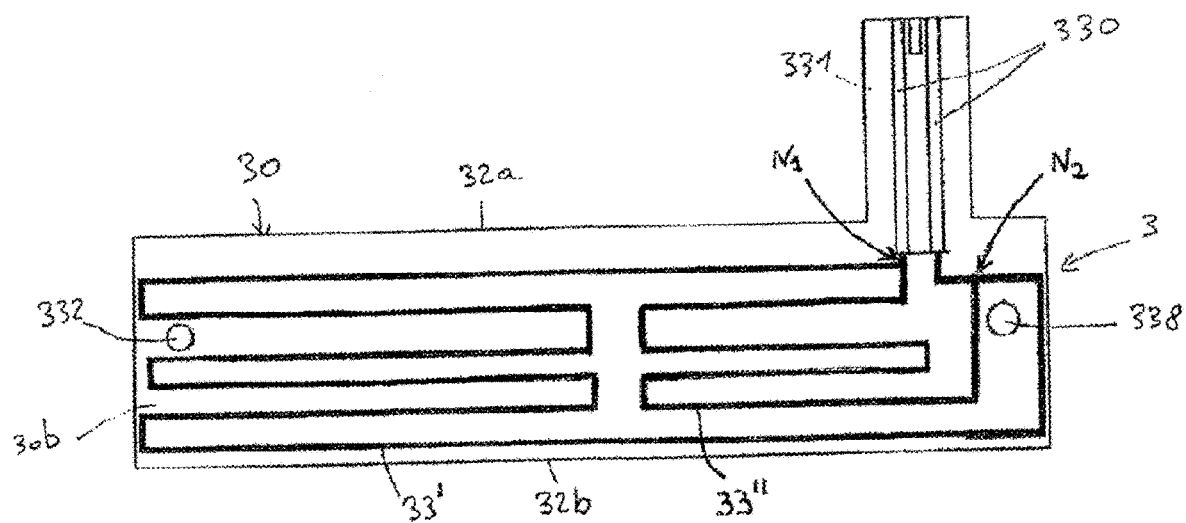
FIG. 18d is a front view of a variant of a pliable, flexible substrate forming the measuring vessel, with said substrate being flat.

In another embodiment variant shown in FIG. 18d, the heating filaments form two resistive sub-assemblies 33' and

33" electrically connected in parallel. Nodes $N_1$ and $N_2$ connect these two resistive sub-assemblies 33', 33" which occupy two separate areas of flexible substrate 30 having substantially identical surface areas. The surface density of the heating filaments is substantially identical in these two areas such that the two resistive sub-assemblies 33' and 33" advantageously have the same static resistance values (with no blowing). Consequently, homogeneous heating of chamber 3 in order to reach the temperature setting is easier than with substrate 30 of FIG. 18c. Under dynamic conditions, the temperature imbalance induced by the exhaled air between inlet 332 and outlet 338 of chamber 3 results in a greater variation of the resistance of resistive sub-assembly 33' (located on the side of inlet 332) compared to that of resistive sub-assembly 33" (located on the side of outlet 338). The parallel electrical connection of these two resistive sub-assemblies compensates for this imbalance by injecting electrical current (at one of nodes $N_1$ or $N_2$) in the resistive sub-assembly having a lower electrical resistance. This configuration allows the heating of chamber 3 to be self-regulated and makes the temperature thereof continuously homogeneous under both static and dynamic conditions, which is not the case with the variants of FIGS. 18a and 18c.

The non-limiting example of FIG. 10d only shows the parallel connection of two resistive sub-assemblies, but it may be extended to multiple resistive sub-assemblies, however without the surface area occupied by each said sub-assembly having to necessarily be identical. Thus, it may be beneficial for the surface density of each resistive sub-assembly not to be identical in order to balance the value of the electrical resistance thereof as a function of the thermal imbalances found in measuring vessel 3.

Heating element 33 is connected to conducting wires 330, which are integrated into a strip 331 of substrate 30 which protrudes from the core of said substrate. Wires 330 are intended to be connected to a battery pack 7. In practice, the power source is determined to deliver a voltage of between 0.1 Volts and 5 Volts, and the power generated by heating element 33 is between 10 mW/cm$^2$ and 10 W/cm$^2$.

Temperature regulation of heating element 33 (and therefore of chamber 3), say in the vicinity of 40° C., can be provided.

In order for the Beer-Lambert law to apply appropriately, chamber 3 must be kept at a constant temperature, and this despite the external heating of chamber 3 caused by the assembly of electronic components in control unit 9 and in measurement means 34, 35, as well as the cooling of the inside of chamber 3 when blowing occurs. It therefore appears to be advantageous to regulate the temperature of chamber 3.

Direct checking of the temperature of chamber 3 by one or more temperature sensors (type PT100, thermistor, SAW, etc.) placed therein could have been considered. However, a temperature sensor can only take a spot measurement of the temperature in the chamber. In practice, temperature regulation is not efficient with a single temperature point. A plurality of temperature sensors distributed along chamber 3 must therefore be provided. However, this solution is costly and requires difficult management of the measured temperatures. In addition, temperature sensors are relatively large and their presence would impact the compactness of device A.

To overcome these technical problems, the temperature of chamber 3 is preferably regulated without a temperature sensor placed therein. Once resistive heating element 33 has been electrically connected to control unit 9, it therefore serves both to produce the energy to heat measuring vessel 3 and, at the same time, to measure the average temperature of the chamber. This solution differs from the known solutions of the prior art in that it combines the two functions of heating and measuring the temperature of chamber 3 in a single component, that is, resistive heating element 33.

The electrical resistance of resistive heating element 33 is used to find the average temperature of chamber 3. When measuring the concentration of an exhaled breath fluid component, the temperature of measuring vessel 3 must be regulated continuously around a target temperature corresponding to a resistance setting of resistive heating element 33. Control unit 9 regulates the electrical power injected into resistive heating element 33 thanks to a negative feedback loop based on real-time measurement of the resistance of said element and the objective of reaching the resistance setting corresponding to the target heating temperature. More specifically, control unit 9 contains a microprocessor 90 (FIG. 20) provided with an acquisition system that measures the amperage, and therefore the resistance, of resistive heating element 33 in real time. The negative feedback loop is provided by a PID (acronym for "Proportional-Integral-Derivative") regulator or any other means of regulation known to a person skilled in the art.

This method of regulation has the advantage of being much more accurate and less costly than the method using temperature sensors. In addition, when a user blows into mouthpiece 1a, the inlet of chamber 3 is cooled by the flow of breath fluid. The regulation method used makes it possible to rebalance the heating temperature between the inlet and outlet of chamber 3 very quickly so that a homogeneous temperature is obtained throughout said chamber (from the inlet to the outlet).

Substrate 30 is made in the shape of a tube in order to constitute measuring vessel 3. Substrate 30 is rolled manually or automatically so as to form a cylindrical tube. The length of chamber 3 thus formed is between 5 mm and 200 mm, preferably equal to or less than 100 mm. The inside diameter thereof is less than 15 mm, for example between 4 mm and 15 mm. If chamber 3 does not have a circular cross-section but rather a square, rectangular, ellipsoid, or other polygon-shaped cross-section, substrate 30 is folded or rolled so as to form chamber 3 having that particular cross-section. Substrate 30 is designed so that the reflective metal material forms the inside surface of chamber 3. This arrangement optimizes the lengths of the optical paths in chamber 3 while retaining a sufficient quantity of light up to the receiver described later in the description. The result is that measuring vessel 3 can be relatively short.

When chamber 3 is being shaped, substrate 30 naturally has a tendency to unroll (or unfold) in order to return to its original flat shape. To prevent this, substrate 30 comprises two opposing longitudinal edges 32a, 32b that are secured to each other by bonding or welding so as to maintain the shape of said substrate in the form of a tube. The two longitudinal ends of edges 32a, 32b can be placed edge-to-edge and attached by bonding, welding, etc. According to a preferred embodiment, one of edges 32a has a free strip 320, shown in FIG. 18b, without any resistive heating element 33. This strip 320 is continuous and runs the entire length of substrate 30. For example, the width thereof is between 2 mm and 5 mm. Strip 320 is used as a bonding area. When substrate 30 is in the shape of a tube, strip 320 covers opposite edge 32b. In this overlap area, the thickness of chamber 3 is therefore double. However, since strip 320 does not have any resistive heating element 33, resistive heating element 33 is not doubled in this overlap area.

In this configuration, the surface density of the filaments in resistive heating element 33 may vary advantageously along transverse axis Y"-Y" orthogonal to axis X"-X". Thus, said density is different at the center of side 30*b* of item 3 and on the edges (on edge 32*b* and on the inside edge of free strip 320, which is opposite edge 32*a*). Homogeneous heating of chamber 3 is therefore obtained without an area of overheating or thermal dissipation associated with the overlap area.

In an embodiment variant, the two longitudinal edges 32*a*, 32*b* of substrate 3 are not secured to each other. Substrate 3 is shaped like a tube and is then inserted into another tube that is preferably not a metal and/or thermal conductor, such as a thin tube made of polyimide (for example: Kapton®), polyepoxide, polyester, fiberglass-reinforced epoxy resin, aluminum substrate (for example: COOL-CLAD® substrate marketed by AI TECHNOLOGY), and so on.

According to yet another embodiment variant, the two longitudinal edges 32*a*, 32*b* of substrate 3 are not secured to each other. Substrate 3 is shaped like a tube without attachment of longitudinal edges 32*a*, 32*b*. Enclosure 2 is made of a single-piece casing comprising an arrangement defining a housing into which substrate 3 thus shaped like a tube is inserted.

Measuring vessel 3 and/or the temperature regulation method thereof may obviously be used in other types of measurement instruments. Those embodiments, however, are not covered by the present claimed invention.

When chamber 3 is shaped like a tube, the tube is open at both ends. The measurement means depends on the gas being analyzed. A means of photometric measurement determining the concentration of the gas is preferably used. In reference to FIGS. 4, 5, and 6, an infrared radiation emitter 34 is installed at one end 3*a* of chamber 3 so that an infrared radiation passes through said chamber. Emitter 34 advantageously emits in wavelengths of between 2 μm and 15 μm. Emitter 34 is advantageously coupled to a cone-shaped optical reflector (not shown) making it possible to increase the intensity of infrared radiation emitted and to concentrate that radiation in chamber 3. An infrared radiation detector 35 is installed at opposite end 3*b*. Emitter 34 and detector 35 are of the type known to a person skilled in the art. For example, emitter 34 may consist of an MEMS and detector 35 may consist of a pyroelectric detector.

When the breath fluid flows into chamber 3 between the two ends 3*a*, 3*b*, said fluid is capable of cooling emitter 34 and/or detector 35, which may disrupt the measurements. To remedy this, a sealed chamber or window is preferably placed in front of emitter 34 and another sealed chamber or window is placed in front of detector 35. These chambers or windows are impermeable to the breath fluid such that said fluid cannot come into contact with emitter 34 and detector 35. Advantageously, each chamber or window is formed by a ring 36 that fits into the respective end 3*a*, 3*b* of chamber 3 and inside which is inserted a transparent lens or disk, made for example of glass or any other material with maximum transparency at the infrared wavelengths useful for measuring the concentration of the component of interest in the exhaled breath fluid.

In an embodiment variant not shown, the positions of emitter 34 and detector 35 are reversed, so that emitter 34 is located at the chamber inlet and detector 35 is located at the chamber outlet near hole 338.

According to a feature of the invention, chamber 3, measurement means 34, 35, pumping means 8, and control unit 9 are grouped together on a common substrate 4*a*, so as to form a grippable unitary assembly. This unitary assembly is installed removably in the housing of enclosure 2. These various means can therefore be easily assembled outside enclosure 2 on removable common substrate 4*a*, such as on a workbench. The operator can therefore install components, secure them, and connect them in a much more accessible work space than that defined by the body of enclosure 2. As a result, installation of the various means is faster than with the aforementioned prior art. The operator needs only to insert the unitary assembly thus formed into enclosure 2 to finalize the manufacturing of device A. Likewise, if one of the electronic components fails, the operator simply has to remove the defective unitary assembly from enclosure 2 and replace it with another unitary assembly in working order. The down time of device A is therefore considerably reduced. The defective unitary assembly can undergo troubleshooting and repair at a later time without impacting the use of device A.

Figure 4:
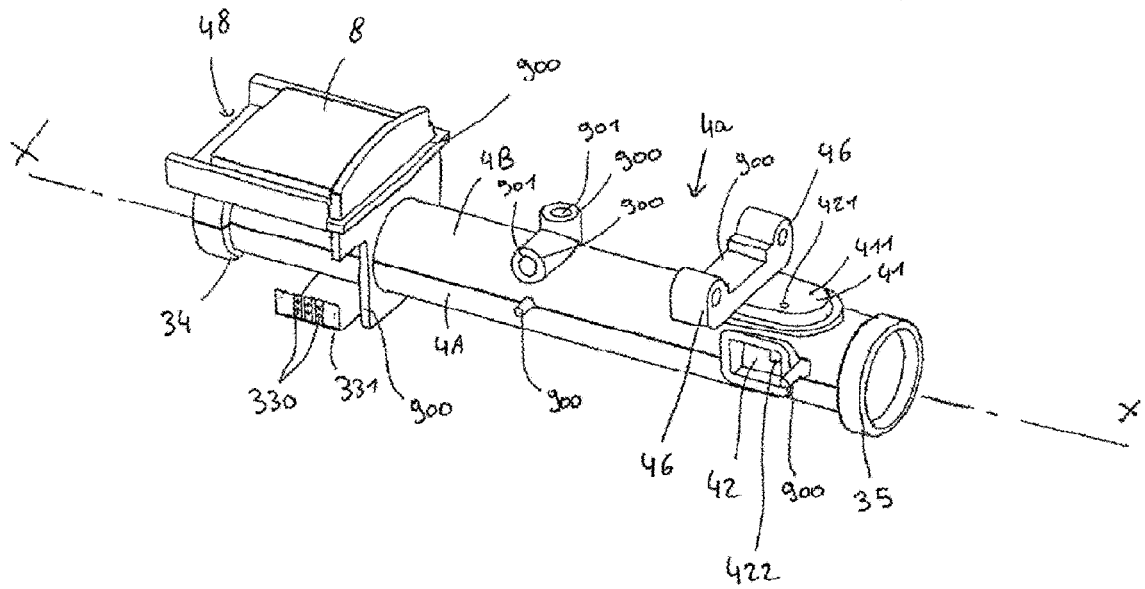
Figure 5:
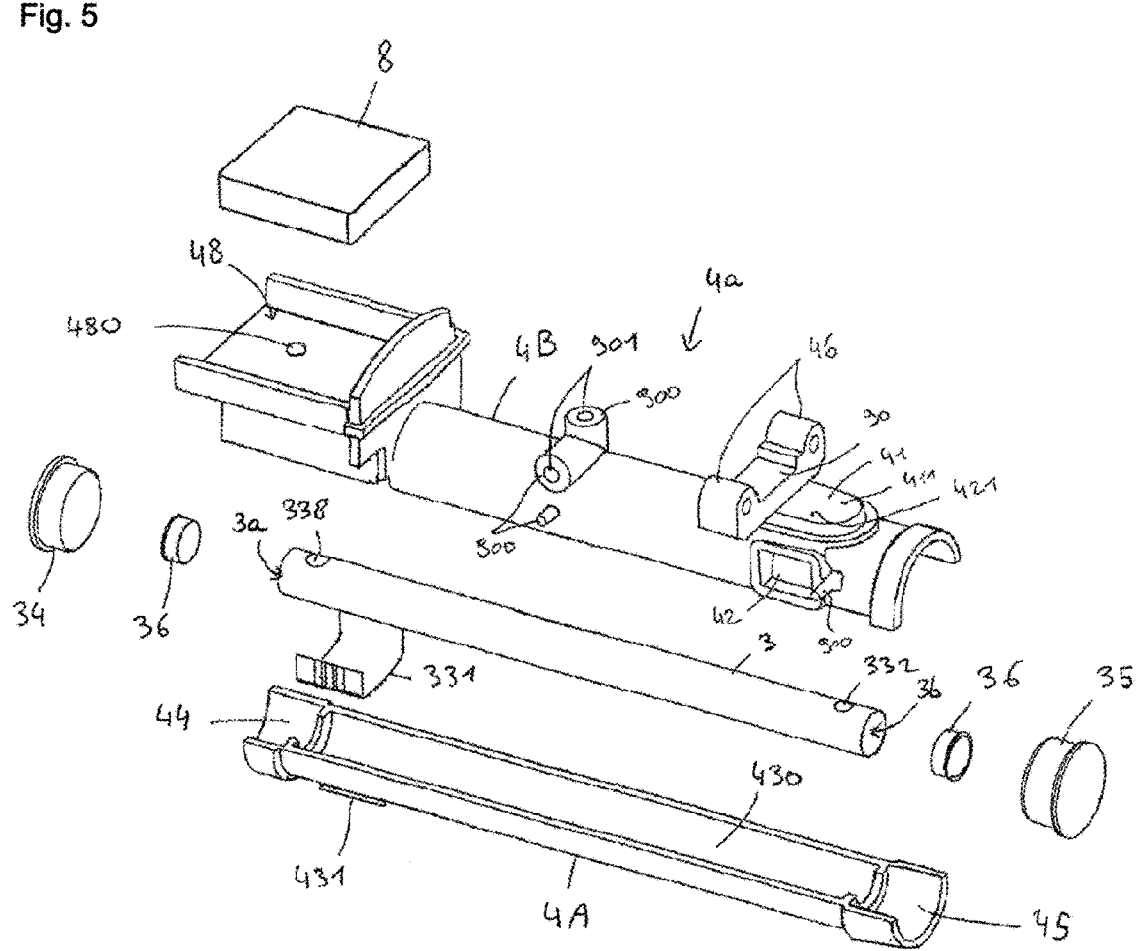
FIG. 5 is an exploded perspective view of the common substrate in FIG. 4 with a measuring vessel in the form of a tube.
Figure 6:
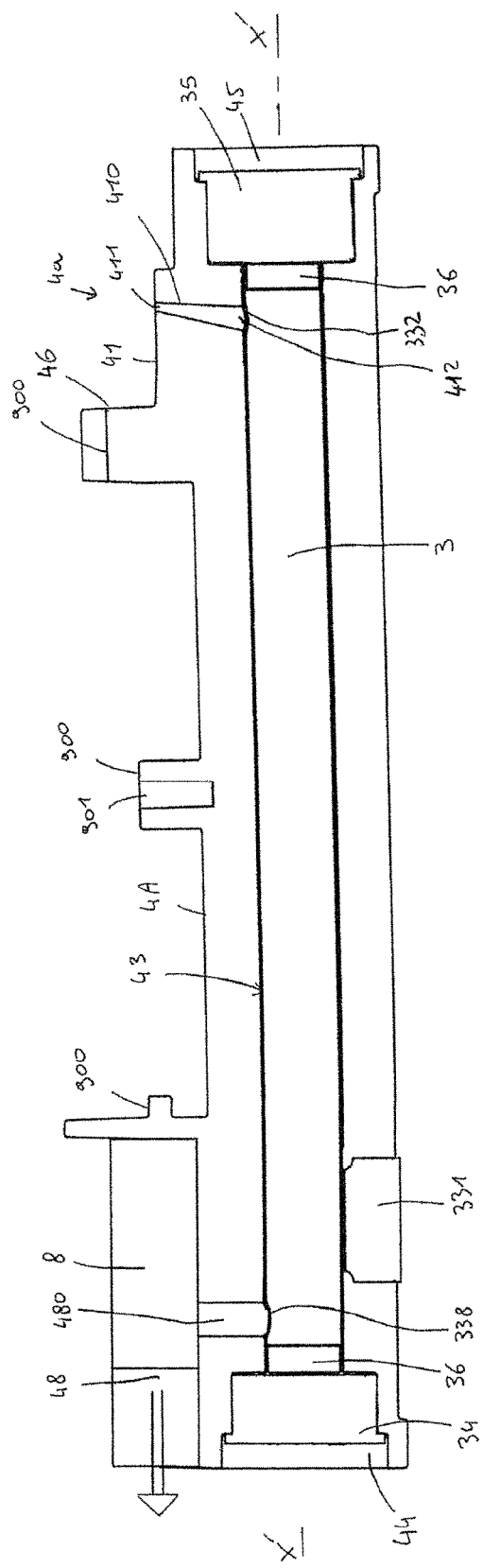
FIG. 6 is a longitudinal cross-sectional view of the common substrate in FIG. 4 on which the measurement means and the pumping means are installed.

In FIGS. 4, 5, and 6, common substrate 4*a* is in the form of an elongated part having a longitudinal axis X'-X' (which also coincides with the longitudinal axis of chamber 3). Common substrate 4*a* is made of a rigid material, such as plastic (e.g. PVC, ABS, PC), carbon, composite material, and so on. It may be made by molding, extrusion, or by any other method suitable for a person skilled in the art. It may require a special surface treatment, particularly a flame-retardant treatment.

In FIG. 5, common substrate 4*a* is made by assembling two parts 4A, 4B having a mating surface parallel to axis X'-X'. Parts 4A, 4B are held together after assembly by a mechanical attachment (screws, catches, etc.), thermal fastening (welding, etc.), or a chemical attachment (bonding, etc.).

Each of parts 4A, 4B has an additional arrangement in the form of cradle 430 or half-tube which, when said parts are assembled, forms a tubular housing 43 in which chamber 3 is installed. This tubular housing 43 has an opening 431 in the form of a slit through which strip 331 of substrate 30 comes out of said housing.

Other housings 44 and 45 are made at the ends of housing 43 to receive emitter 34 (and sealed window 36 thereof) and detector 35 (and sealed window 36 thereof), respectively. Depending on the type of measurement means used, a single dedicated housing can be provided.

A common substrate 4*a* in two parts 4A, 4B facilitates the assembly of chamber 3 and of emitter 34 and detector 35. Chamber 3 in the shape of a tube is placed in cradle 430 of lower part 4A. Next, emitter 34 is placed in the cradle forming housing 44, and detector 35 is placed in the cradle forming housing 45. Sealed chambers or windows 36 can be assembled with ends 3*a*, 3*b* of chamber 3 ahead of time or placed in position during the installation of emitter 34 and detector 35. When components 3, 34, 35, and 36 are installed in lower part 4A, upper part 4B is installed to hold them in place.

Installation of components 3, 34, 35, and 36 is also possible using a unitary common substrate 4*a* provided with tubular housing 43, at the ends of which the other tubular housings 44 and 45 are provided. Assembly then proceeds by inserting chamber 3 in housing 43, then placing chambers or windows 36 at each end of said chamber, and lastly by installing emitter 34 and detector 35.

In reference to FIGS. 6 and 9, common substrate 4*a* comprises a drill hole 410 leading into housing 43 in which chamber 3 is installed. More specifically, drill hole 410 has a first hole 411 leading into an external wall 41 of common substrate 4*a*, and a second hole 412 leading into housing 43 at the location of a hole 332 (FIGS. 18*a* and 18*b*) made in substrate 30 of chamber 3. Drill hole 410 is thus in fluid communication with chamber 3. Drill hole 410 may have a constant cross-section. Drill hole 410, however, is preferably conical with a flare of the cone toward chamber 3, that is, the diameter of first hole 411 is less than the diameter of second hole 412. This configuration greatly reduces the speed of the breath fluid at the inlet of chamber 3. By reducing this speed, the airflow problems are limited and the turbulence in chamber 3 is reduced (said turbulence is capable of slowing the filling of said chamber and of decreasing the accuracy of the concentration measurement of the component of interest in the exhaled breath fluid). A cone-shaped drill hole 410 thus allows for a more homogeneous distribution of the fluid in chamber 3. Satisfactory results are also obtained with a cylindrical drill hole 410, but with poorer performance in terms of filling speed and homogenized distribution of the fluid in chamber 3.

With specific reference to FIG. 9, common substrate 4a comprises another drill hole 420 leading into a chamber 42 made in said substrate. This chamber 42 is more visible in FIG. 4a. A pressure sensor (not shown) is installed in chamber 42. This pressure sensor is of the type known to a person skilled in the art and is connected to control unit 9 described later in the description. Drill hole 420 has a first hole 421 leading to wall 41 of common substrate 4a, and a second hole 422 leading into chamber 42. Wall 41 therefore has the two holes 411 and 421.

As shown in FIG. 9, when mouthpiece 1a is installed in opening 21A, outlet 112a comes out above wall 41 of common substrate 4a such that it is in fluid communication with first drill hole 410 and with second drill hole 420. Core 11 of mouthpiece 1a, the inside wall of tube 2A, and wall 41 of common substrate 4a can be arranged together and cooperate to delimit a chamber in which holes 112a, 411, and 421 are located. The sample of exhaled breath fluid that comes out of mouthpiece 1a through outlet 112a thus enters drill hole 410 to enter measuring vessel 3, and enters drill hole 411 to enter chamber 42. The pressure measurement in chamber 42 is used by control unit 9 to deduce the value of the breath fluid flow flowing in measuring vessel 3.

Common substrate 4a also comprises a housing 48 in which pumping means 8 is installed. Pumping means 8 is in the form of a flat fan installed in housing 48. It comprises a drill hole 480 leading into housing 43 where chamber 3 is installed such that the housings are in fluid communication. More specifically, drill hole 480 has a first hole which leads into housing 43 at the location of a hole 338 (FIGS. 10a and 10b) made in substrate 30 of chamber 3. Drill hole 480 also has a second hole leading into housing 48 at the location of fan 8.

In FIGS. 18a and 18b, holes 332 and 338 are located at a lateral edge of substrate 30, respectively. The dimensions thereof are adjusted to the diameters of drill holes 410 and 480.

Figure 3A:
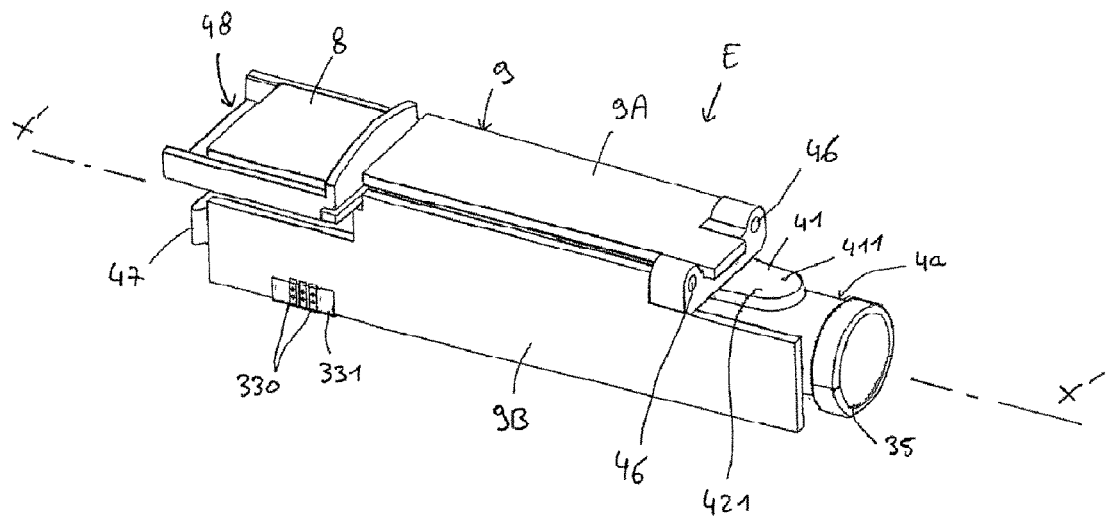
FIG. 3a is a front perspective view of a unitary assembly according to a first embodiment.
Figure 3B:
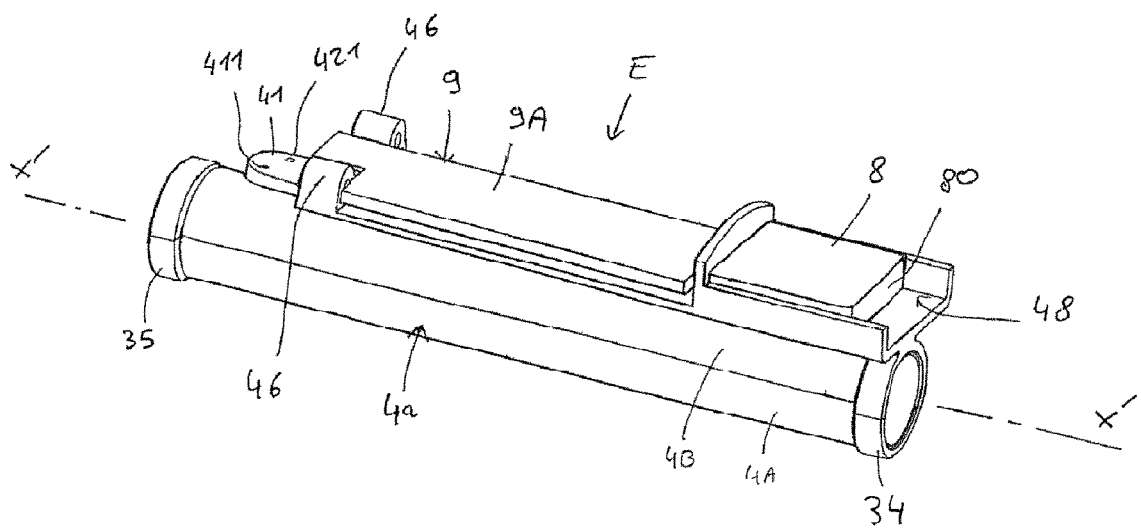
FIG. 3b is a rear perspective view of the unitary assembly in FIG. 3a, FIG. 4 is a perspective view of a common substrate according to a first embodiment.

As shown in FIG. 3b, fan 8 comprises an outlet 80 through which the breath fluid is expelled. This outlet 80 is configured so that the direction of breath fluid expulsion (shown by the double arrow in FIGS. 6a and 6b) is parallel to longitudinal axis X'-X' of chamber 3. The breath fluid is thus extracted into enclosure 2, parallel to the longitudinal axis X-X thereof. This breath fluid thus extracted from the entire length of enclosure 2 until it exits through opening 220B of cap 22B, possibly while cooling, along the way, the other elements incorporated into said enclosure. In addition, the applicant has observed that this expulsion direction avoids any inadvertent back flow of the breath fluid into chamber 3.

In FIGS. 3a and 3b, control unit 9 is in the form of one or more printed circuit boards 9A, 9B containing electronic components (not shown) for monitoring and controlling device A and particularly measurement means 34, 35, as well as pumping means 8. Control unit 9 is also suitable for activating and controlling the heating of chamber 3 and the aforementioned pressure sensor.

Second Embodiment

Figure 10:
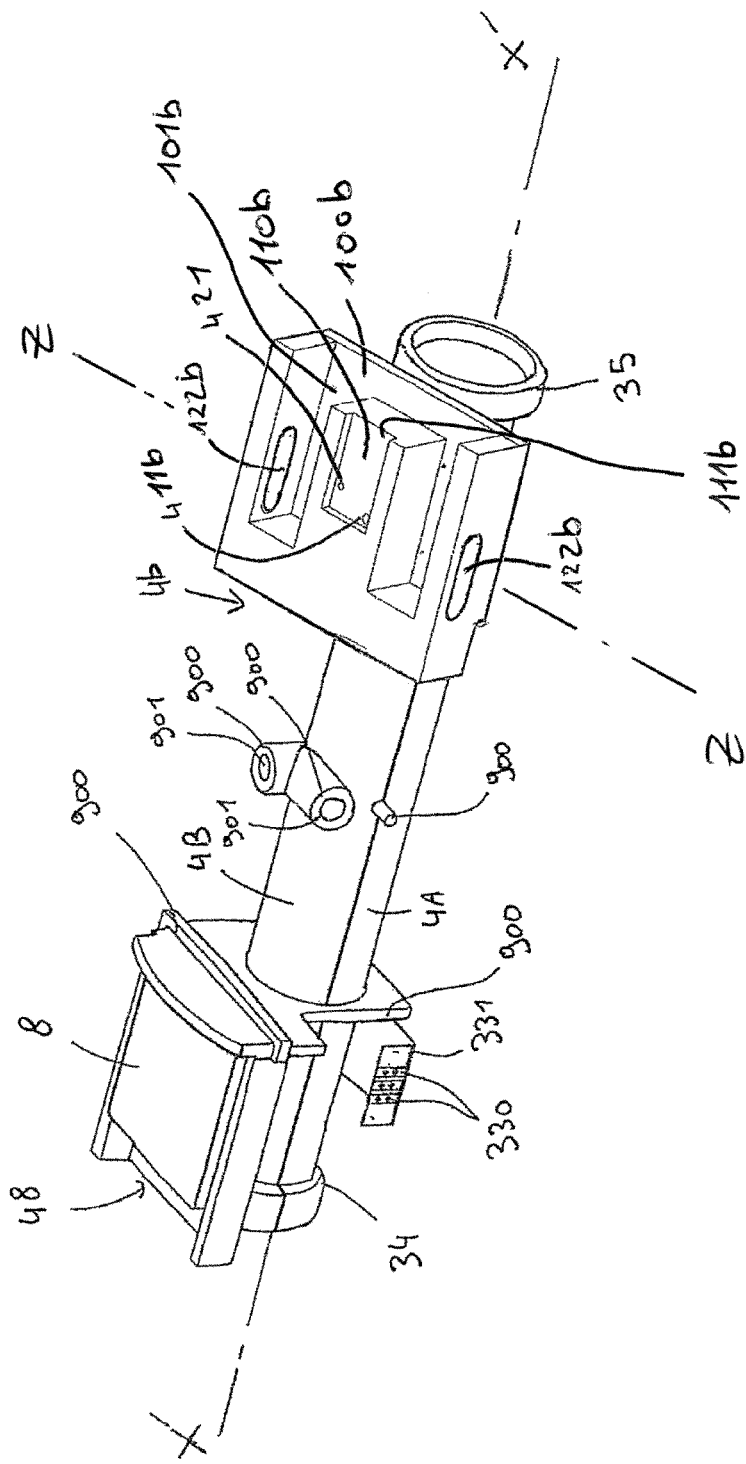
FIG. 10 is a perspective view of a common substrate according to a second embodiment.
Figure 11:
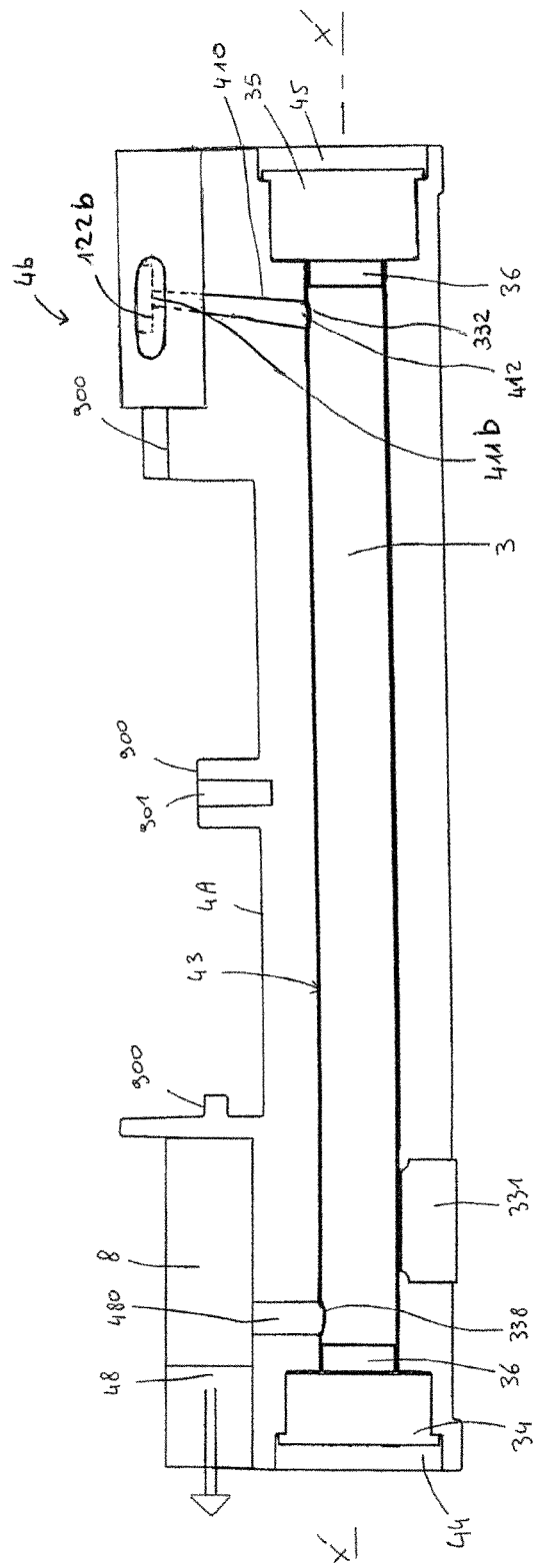
FIG. 11 is a longitudinal cross-sectional view of the common substrate in FIG. 10 on which the measurement means and the pumping means are installed.
Figure 14:
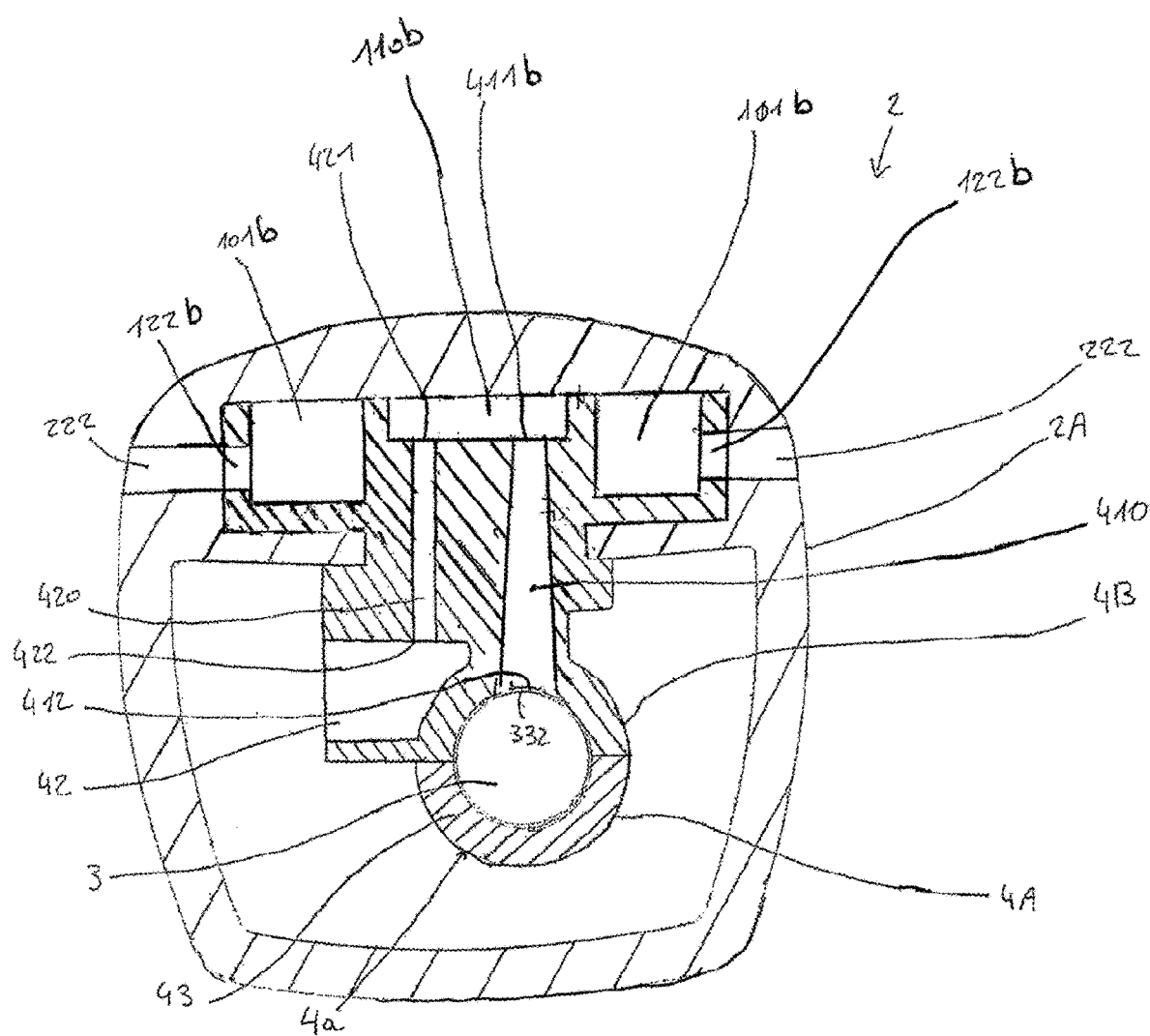
FIG. 14 is a transverse cross-sectional view of the mouthpiece in FIGS. 12 and 13 and of the common substrate in FIGS. 10 and 11, installed in the enclosure.

According to a second embodiment, the two chambers are made in common substrate 4b, as shown in FIGS. 10, 11, and 14. This configuration makes it possible to further simplify the shape of mouthpiece 1b without adversely affecting the accuracy of the breath gas concentration measurement taken in measuring vessel 3.

Figure 12:
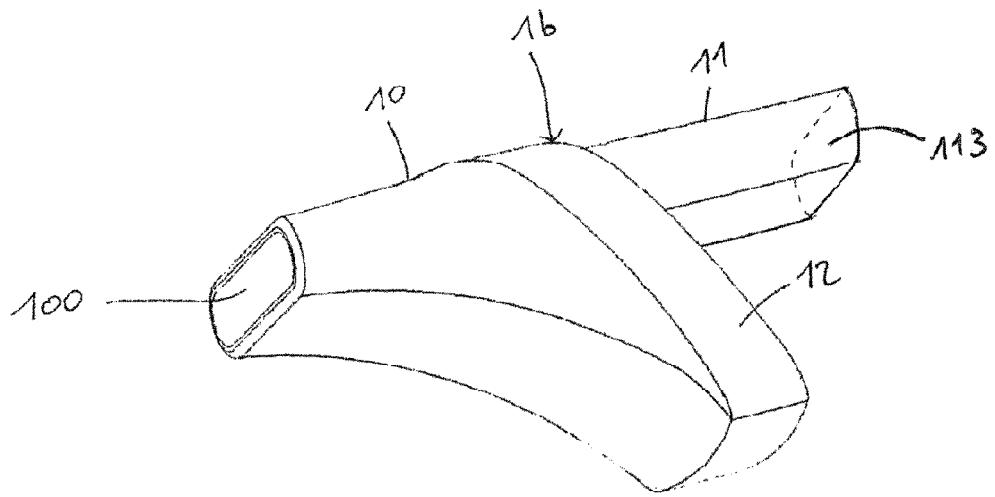
FIG. 12 is a perspective view of a mouthpiece for cooperating with the common substrate of FIGS. 10 and 11.
Figure 13:
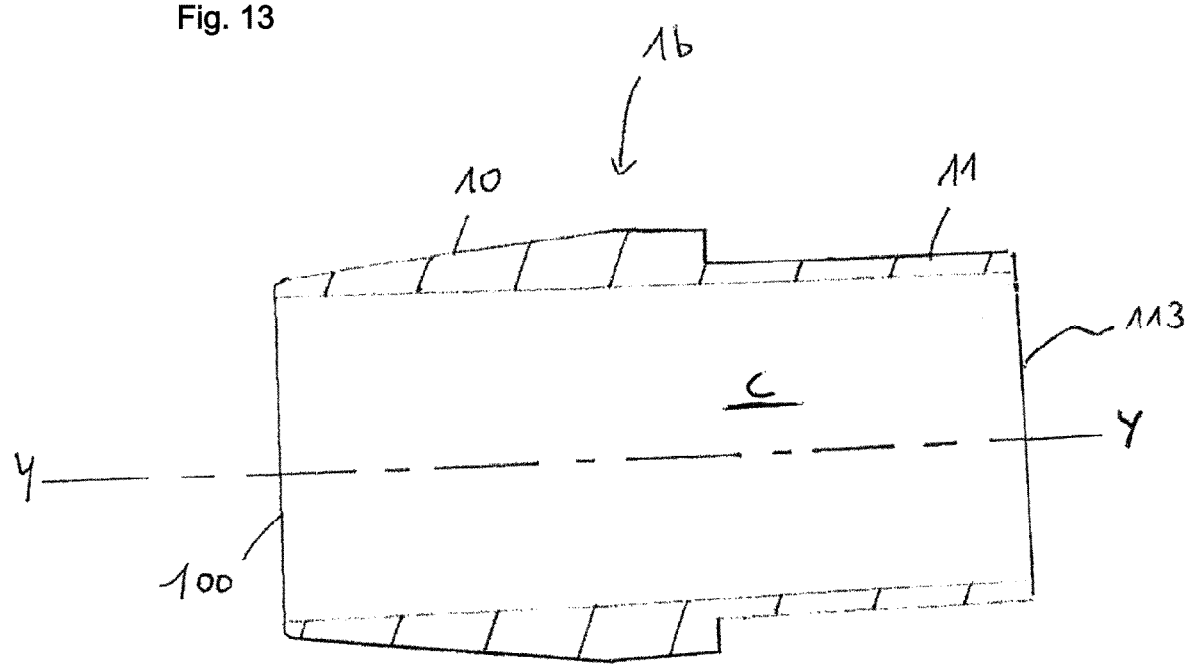
FIG. 13 is a longitudinal cross-sectional view of the mouthpiece in FIG. 12.

In FIGS. 12 and 13, mouthpiece 1b comprises a chamber C equipped with an inlet 100 and an outlet 113. The cross-sections of these two holes are identical or substantially identical. In comparison to mouthpiece 1a of the first embodiment, this configuration reduces the level of complexity, and consequently the number of manufacturing steps, of mouthpiece 1b. It also reduces the quantities of material used to manufacture this part and thus lowers the cost price thereof. However, since the size of outlet 113 is substantially greater than that of outlet 112 of mouthpiece 1a, mouthpiece 1b sends a larger portion of breath fluid to device A. The breath fluid may contain particles that can foul said device. Consequently, in the configuration of FIGS. 12 and 13, it may be advantageous to provide mouthpiece 1b with a filter (not shown) upstream of or at outlet 113 thereof so as to substantially reduce dirt buildup in device A. The term "upstream" refers to the direction of flow of the exhaled breath fluid.

This mouthpiece 1b can be associated with common substrate 4b shown in FIGS. 10 and 11. First chamber 101b and second chamber 110b are made on common substrate 4b upstream of chamber 3. Second chamber 110b is placed inside first chamber 101b.

Second chamber 110b has smaller dimensions compared to first chamber 101b, as in the first embodiment. The two chambers 101b and 110b are open in the upper portion thereof. As shown in FIG. 14, these openings are closed and sealed during the assembly of common substrate 4b with enclosure 2A. First chamber 101b comprises an inlet 100b through which the exhaled breath fluid enters said first chamber. This inlet 100b is adjacent to outlet 113 of mouthpiece 1b and communicates with chamber C when said mouthpiece is installed in enclosure 2. Second chamber 110b also comprises an inlet 111b leading into first chamber 101b.

As in the first embodiment, common substrate 4b comprises a first drill hole 410 leading into chamber 3 and a second drill hole 420 leading into chamber 42.

Drill hole 410 has a first hole 411b leading into second chamber 110b and a second hole 412 leading into housing 43, at the location of hole 332. Drill hole 410 thus puts second chamber 110b in fluid communication with chamber 3. Hole 411b is the outlet through which the portion of exhaled breath fluid flowing into second chamber 110b passes (equivalent to hole 112 of mouthpiece 1a in the first embodiment).

Drill hole 420 has a first hole 421 leading into second chamber 110b and a second hole 422 leading into chamber 42.

The external side walls of first chamber 101b comprise outlets 122b through which the portion of exhaled breath fluid not flowing into measuring vessel 3 is expelled into the ambient air. For the same reasons as those mentioned previously in reference to the first embodiment, these outlets 122b are lateral holes oriented in a direction Z-Z that is perpendicular to alignment Y-Y of holes 100, 113, 100b, and 110b. In reference to FIG. 14, when substrate 4a is installed in tube 2A, outlets 122a are opposite holes 222 arranged laterally on enclosure 2.

Also, for the same reasons as those mentioned previously in reference to the first embodiment, and as shown in FIG. 10, inlet 111b of second chamber 110b is advantageously located upstream of outlets 122b. And the lateral walls of second chamber 110b preferably have dimensions along axis Y-Y that are greater than the dimensions of outlets 122b.

When mouthpiece 1b is installed in opening 21A of enclosure 2, first drill hole 410, second drill hole 420, and outlets 122b are in fluid communication with outlet 113 of mouthpiece 1b. Consequently, the distance separating inlet 100 from inlet 411 is typically less than 50 mm This configuration has the advantage of no longer requiring a precise alignment between mouthpiece 1b and common substrate 4b, which loosens the manufacturing tolerances and therefore the cost of the mouthpieces. However, this configuration still requires a precise alignment between common substrate 4b and tube 2A so that outlets 122b are aligned with lateral holes 222.

Third Embodiment

Figure 15:
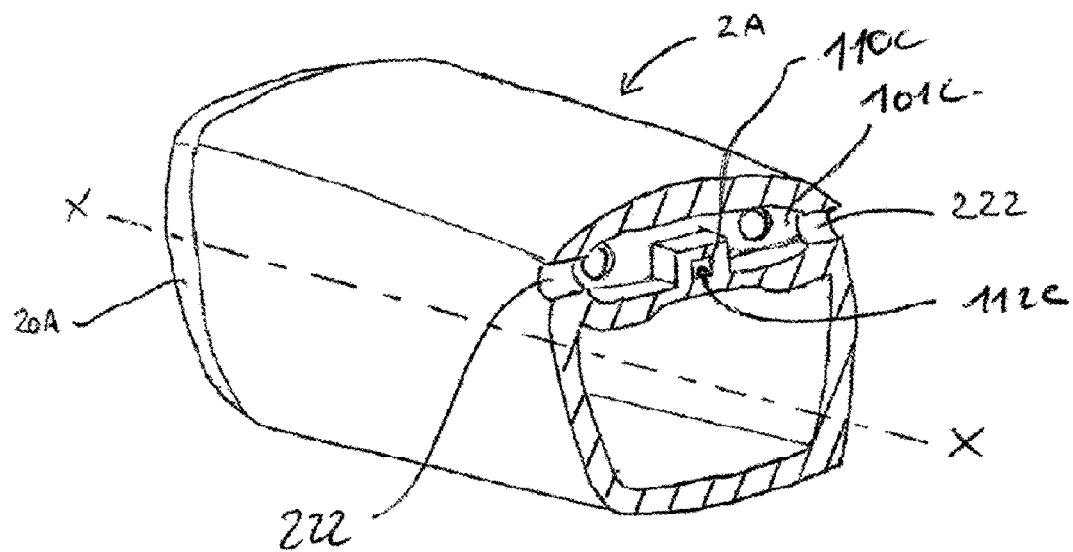
FIG. 15 is a transverse cross-sectional view of an enclosure according to a third embodiment of the invention.
Figure 16:
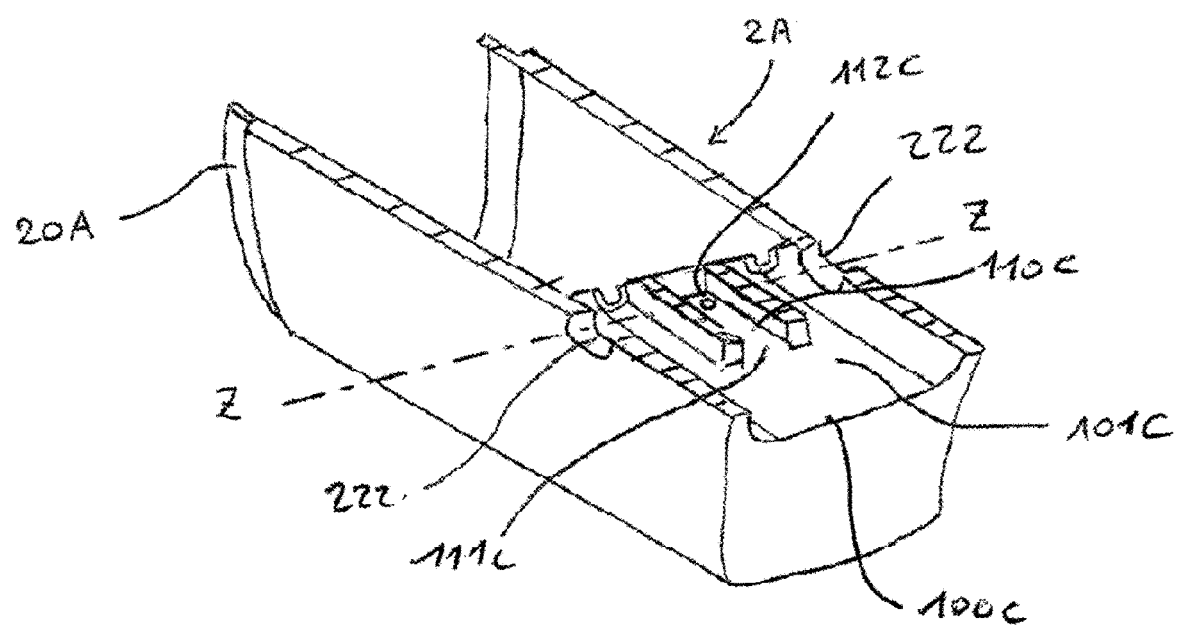
FIG. 16 is a longitudinal cross-sectional view of an enclosure according to FIG. 15.
Figure 17:
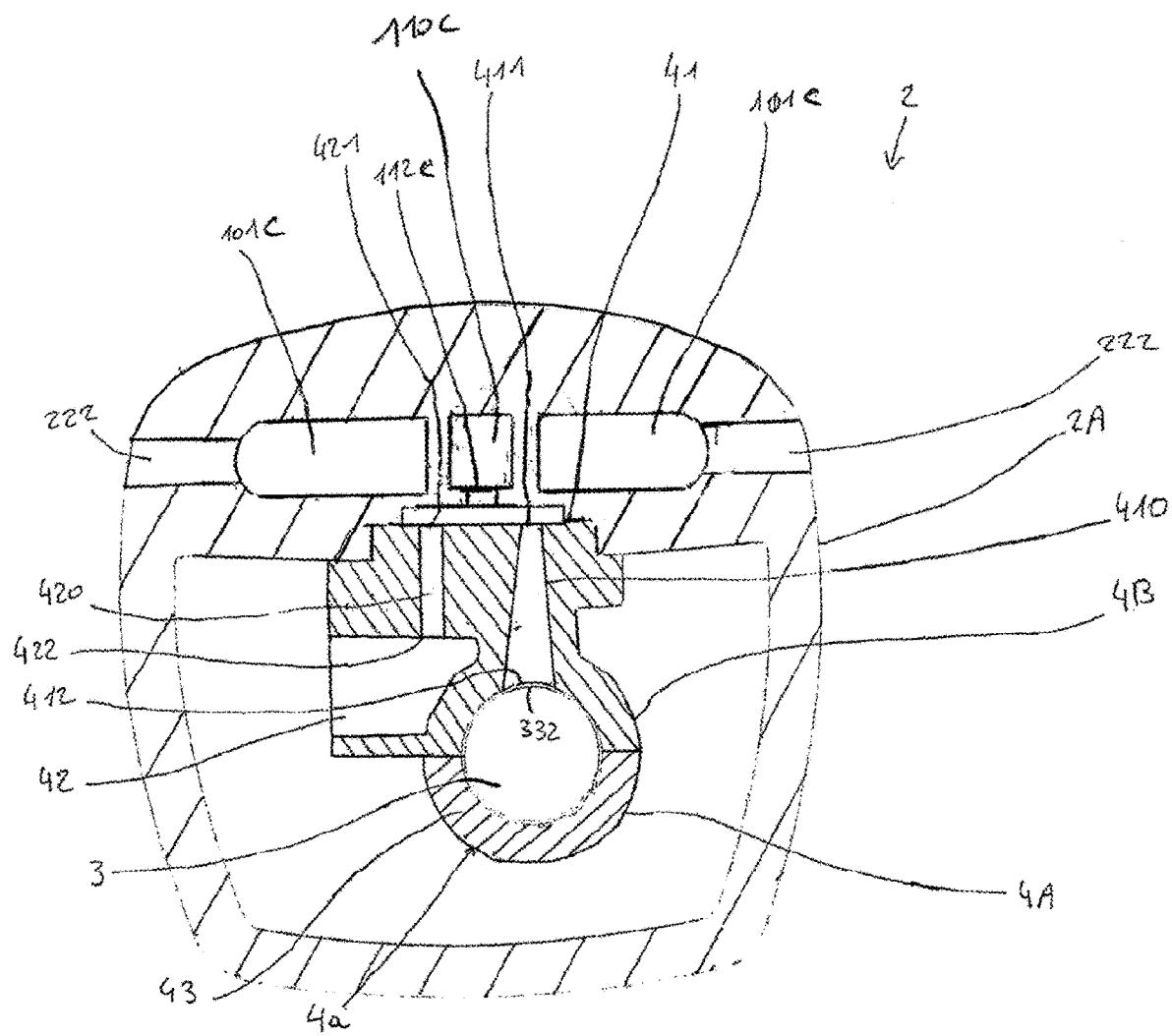
FIG. 17 is a transverse cross-sectional view of the common substrate in FIGS. 4 to 6, installed in the enclosure of FIGS. 15 and 16.

According to a third embodiment, the two chambers are made in enclosure 2, as shown in FIGS. 15 to 17. This configuration simplifies the design insofar as mouthpiece 1b of the second embodiment can be associated with common substrate 4a of the first embodiment, without adversely affecting the accuracy of the breath gas concentration measurement taken in measuring vessel 3.

First chamber 101c and second chamber 110c are made in enclosure 2 and more specifically in tube 2A upstream of chamber 3. Second chamber 110c is placed inside first chamber 101c.

Second chamber 110c has smaller dimensions compared to first chamber 101c, as in the first embodiment and the Second embodiment. First chamber 101c comprises an inlet 100c through which the exhaled breath fluid enters said first chamber. This inlet 100c is adjacent to outlet 113 of mouthpiece 1b and communicates with chamber C when said mouthpiece is installed in enclosure 2. Second chamber 110c also comprises an inlet 111c leading into first chamber 101c.

The portion of exhaled breath fluid flowing into second chamber 110c is extracted through an outlet 112c in fluid communication with measuring vessel 3, as explained later in the description.

The other portion of the exhaled breath fluid that is not flowing into second chamber 110a is expelled to the ambient air by outlets 222 made in the lateral walls of tube 2A and which lead directly to first chamber 101c.

For the same reasons as those mentioned previously in reference to the first embodiment:
outlets 222 are lateral holes oriented along a direction Z-Z perpendicular to the alignment Y-Y of holes 100, 113, 100c, and 110c;
inlet 111c of second chamber 110c is advantageously located upstream of outlets 222. And the lateral walls of second chamber 110c preferably have dimensions along axis X'-X' that are greater than the dimensions of outlets 222.

As shown in FIG. 17, when mouthpiece 1b is installed in opening 21A, outlet 112c comes out above wall 41 of common substrate 4a such that it is in fluid communication with first drill hole 410 and with second drill hole 420. The inside wall of tube 2A and wall 41 of common substrate 4a can be arranged together and cooperate to delimit a sealed chamber in which holes 112c, 411, and 421 are located. The sample of exhaled breath fluid that comes out of chamber 110c through outlet 112c thus enters drill hole 410 to enter measuring vessel 3, and enters drill hole 411 to enter chamber 42.

Consequently, the distance separating inlet 100 from outlet 112c is typically less than 50 mm Here again, this configuration has the advantage of no longer requiring a precise alignment between mouthpiece 1b, common substrate 4a, and front tube 2A of enclosure 2, which loosens the manufacturing tolerances and therefore lowers the cost of these parts. In addition, an alignment of the longitudinal axis of second chamber 110c with the insertion axis of mouthpiece 1b allows the exhaled breath fluid to follow a direct path between inlet 100 of mouthpiece 1b and outlet 112c of front tube 2A.

Regardless of the embodiment (first, second, or third), in order to accommodate the user's comfort when blowing into device A and/or to vary the volume of breath fluid sampled in measuring vessel 3, it is possible to vary the ratio $R_1$ between the sum $S_{OSE}$ of the average cross-sections of outlets 122a, 122, and 222, and the smallest of the average cross-sections of second chamber 110a, 100b, and 110c $S_{SC}$ or of outlet 112a, 411b, 112c $S_{OS}$, such that $R_1 = S_{OSE}/\min(S_{SC}; S_{OS})$. This ratio $R_1$ is advantageously between 5 and 50 ($5 < R_1 < 50$) such that 2% to 20% of the breath fluid passing through inlet 100 comes out of outlet 112. In other words, 80% to 98% of the exhaled breath fluid in first chamber 101a, 101b, 101c is expelled to the ambient air through outlet 122a, 122b, 222. Advantageously, the size of the various holes or chambers are designed so that the ratio $R_1$ is between 12 and 35.

Figure 20:
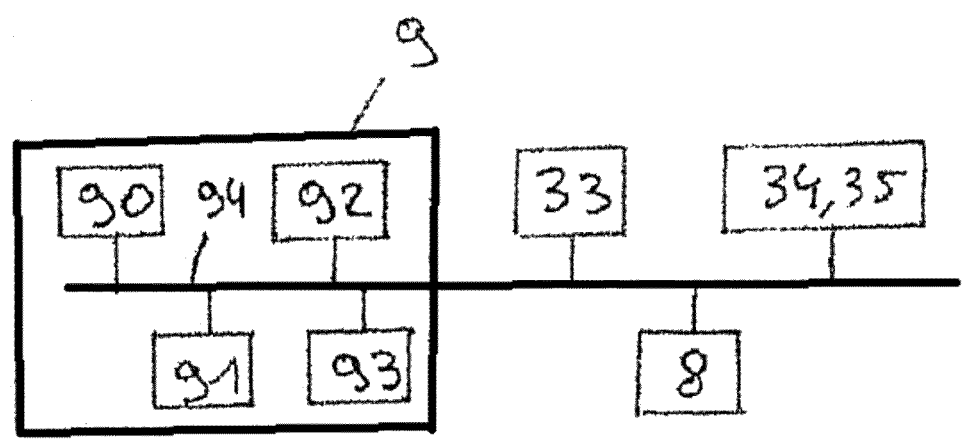
FIG. 20 is a simple illustration of the structure of a control unit used in the invention.

In reference to FIG. 20, control unit 9 comprises one or more processors or microprocessors 90, one or more memories 91, a communication module 92, and possibly a network interface 93, which are connected to each other via a bus 94. One or more computer applications—or computer programs—are stored in memory or memories 91 and the instructions (or code) thereof, when executed by processor or processors 90, carry out the functions of device A. For the sake of clarity, it must be understood in accordance with the invention that "device A does something" means that "the computer application executed by the processor of device A does something." Likewise, "the computer application does something" means "the computer application executed by the processor of device A does something."

Memory or memories 91 must be considered to be a storage device also for storing data and/or data files, such as previous measurements. This memory may be native memory or added memory, such as a Secure Digital (SD) card.

Communication module 92 is for exchanging radio signals transmitted wirelessly using a mobile terminal paired to device A. In order to simplify the design, the radio signals are preferably signals that use a Bluetooth protocol. However, other protocols such as: ISM, Wifi, ANT, ZIGBEE, etc., may be used. The mobile terminal is in the form of a smartphone such as an iPhone® or Samsung Galaxy®, or in the form of another electronic terminal, for example a tablet computer with a touch screen (such as an iPad® or Samsung GalaxyTab® running an operating system such as Windows, Mac, iOS, Android, and so on. Such a mobile terminal is suitable for use by a user, which in practice is the owner of device A.

Network interface 93 is suitable for establishing communication between device A and a remote computer server. Network interface 93 may comprise, for example, a GSM module providing Internet network connectivity to device A. Generally speaking, the function of network interface 93 is to manage connections between device A and an Internet network.

Measurement means 34, 35, pumping means 8, resistive heating element 33 of chamber 3, and the pressure sensor installed in chamber 42 can be connected to common bus 94.

In the appended figures, common substrate 4a, 4b comprises one or more arrangements to receive control unit 9, particularly printed circuit boards 9A, 9B. These arrangements are in the form of edges and/or studs 900 on which boards 9A, 9B rest. These arrangements 900 are preferably distributed over a plurality of sides of the common substrate 4a, 4b so that a plurality of boards 9A, 9B can be secured to said substrate with different orientations. A particularly compact unitary assembly E is thus obtained. Boards 9A, 9B are secured to common substrate 4a, 4b by means of screws that engage with threads 901 made in studs 900 (FIGS. 4 and 5).

To simplify the design, one of boards B preferably holds the aforementioned pressure sensor. Once installed on common substrate 4a, 4b, this board B covers an open side of chamber 42 in such a way that said open side is sealed off from the breath fluid. This coverage is done so that the pressure sensor is housed in chamber 42.

Measuring vessel 3, measurement means 34, 35, pumping means 8, and control unit 9 are therefore grouped together on common substrate 4a, 4b so as to form unitary assembly E. This assembly E can be gripped, meaning that it can be easily handled by an operator.

In reference to FIGS. 2a and 2b, unitary assembly E is installed removably in the housing of enclosure 2, and more specifically inside front tube 2A. This installation is performed very simply by sliding assembly E into tube 2A along axis X-X. Assembly E is advantageously held in position in tube 2A by means of screws 26, which connect to a wall of said tube and engage with threads 46 made in common substrate 4a (FIGS. 2a, 3a, 4, 6).

Other tube 2B is suitable for receiving an electric battery pack 7 for supplying power to device A, and more specifically: means of information 21, measurement means 34, 35, pumping means 8, and control unit 9. Battery pack 7 is also suitable for providing power to resistive heating element 33 if this item is integrated into substrate 30 of chamber 3 and used. Battery pack 7, for example, is in the form of an assembly of one or more batteries capable of delivering between 2 Volts and 24 Volts. Battery pack 7 can also be in the form of a rechargeable battery pack such as those used in Smartphones, in which case enclosure 2 is provided with connections for connecting device A to the mains in order to recharge said battery pack.

Battery pack 7 is advantageously sized to provide at least 75 measurement cycles at an ambient temperature of between 0° C. and 50° C. The choice of components (measurement means 34, 35, pumping means 8, heating element 33, control unit 9, means of information 21) and the means of management thereof during a measurement cycle can make it possible to minimize the electrical power required for each measurement cycle. In particular, the minimal thickness of the layer of reflective metal material on measuring vessel 3 limits the thermal inertia of the assembly and therefore allows said chamber to be heated very quickly. The electrical power needed to heat up said chamber is therefore optimized.

In reference to FIGS. 2a and 3a, battery pack 7 is connected to a conductive flexible blade 70 that is suitable for coming into contact with a conductive blade 47 arranged on common substrate 4a, 4b and more specifically connected to board 9B. Contact between blades 70 and 47 is made when tubes 2A, 2B are assembled, said contact enabling an electrical power supply to unitary assembly E.

Tube 2B is also suitable for receiving means of information 21 and on/off button 20. To that end, tube 2B has an opening 221B made in the wall thereof, said opening being configured to receive a substrate 221 to which button 20 and screen 21 are secured.

The operation of device A will now be described in greater detail.

The user presses button 20 to turn on device A.

The user blows into mouthpiece 1a, 1b through opening 100. The flow of the breath fluid enters first chamber 101a, 101b, 101c. Most of the breath fluid is released to the ambient air via lateral outlets 122a, 122b, 222.

A sample of the breath fluid enters second chamber 110a, 110b, 110c and exits said second chamber under pressure via outlet 112a, 411b, 112c.

This sample of breath fluid enters measuring vessel 3 through passage 410. It should be noted that the blowing pressure of the breath fluid in mouthpiece 1a, 1b is what forces the sample to flow into the chamber and not a possible partial vacuum created in said chamber by pumping means 8. The flow of the breath fluid flowing into chamber 3 may therefore vary depending on the user. Consequently, it is of interest to measure, in chamber 42, the pressure of the breath fluid flowing in chamber 3 in order to calculate the flow rate of said fluid.

The concentration of one or more components of the breath fluid gas flowing in chamber 3 is measured by measurement means 34, 35.

The breath fluid exits measuring vessel 3 through drill hole 480, pumping means 8 serving for the removal thereof. Pumping means 8 is used more so to compensate for the pressure losses and to clear chamber 3 than to create a partial vacuum in said chamber for sampling the breath fluid. The breath fluid passes through enclosure 2 and is then released to the ambient air via opening 220B.

The gas concentration measured by measurement means 34, 35 is processed by control unit 9 as a function of the pressure measured in chamber 42, and therefore the flow rate, so as to calculate the concentration of the component in the breath fluid gas (for example: the mass of the component per liter of exhaled gas). The concentration value thus calculated can then be displayed on screen 21.

Device A can also be controlled from a mobile terminal (smartphone, tablet, etc.) paired to with device. Communications between device A and the terminal take place by means of the aforementioned communication module 92. The user may come to install one or more computer applications on his/her mobile terminal to implement all or a portion of the invention, depending on said terminal, particularly the pairing procedure. These computer applications can be preinstalled on the mobile terminal. However, the user has the option of looking for these computer applications in an online store such as Google Play®, Runes®, or a dedicated Internet site, and downloading them to his/her mobile terminal.

For the sake of clarity, according to the invention it must be understood that "the mobile terminal does something"

means "the computer application executed by a processor of the mobile terminal does something". Likewise, "the computer application does something" means "the computer application executed by a processor of the mobile terminal does something."

When this computer application is launched from the mobile terminal, a plurality of graphical interfaces are displayed on a screen of said terminal so as to monitor, guide, and/or inform the user. These graphical interfaces are shown in FIGS. 19a to 19i. They apply to a use of device A as a breathalyzer or breath tester.

Figure 19A:
FIG. 19a shows a graphical interface that can be seen on a mobile terminal paired with a device according to the invention.

FIG. 19a: the computer application displays a selectable button 600 on the screen of terminal T, which is used to start a measurement. Selection of button 600 may be optional. Indeed, terminal T can communicate continuously with device A and as soon as a breath is detected by the pressure sensor installed in chamber 42, said terminal automatically displays the screen of FIG. 19b.

Figure 19B:
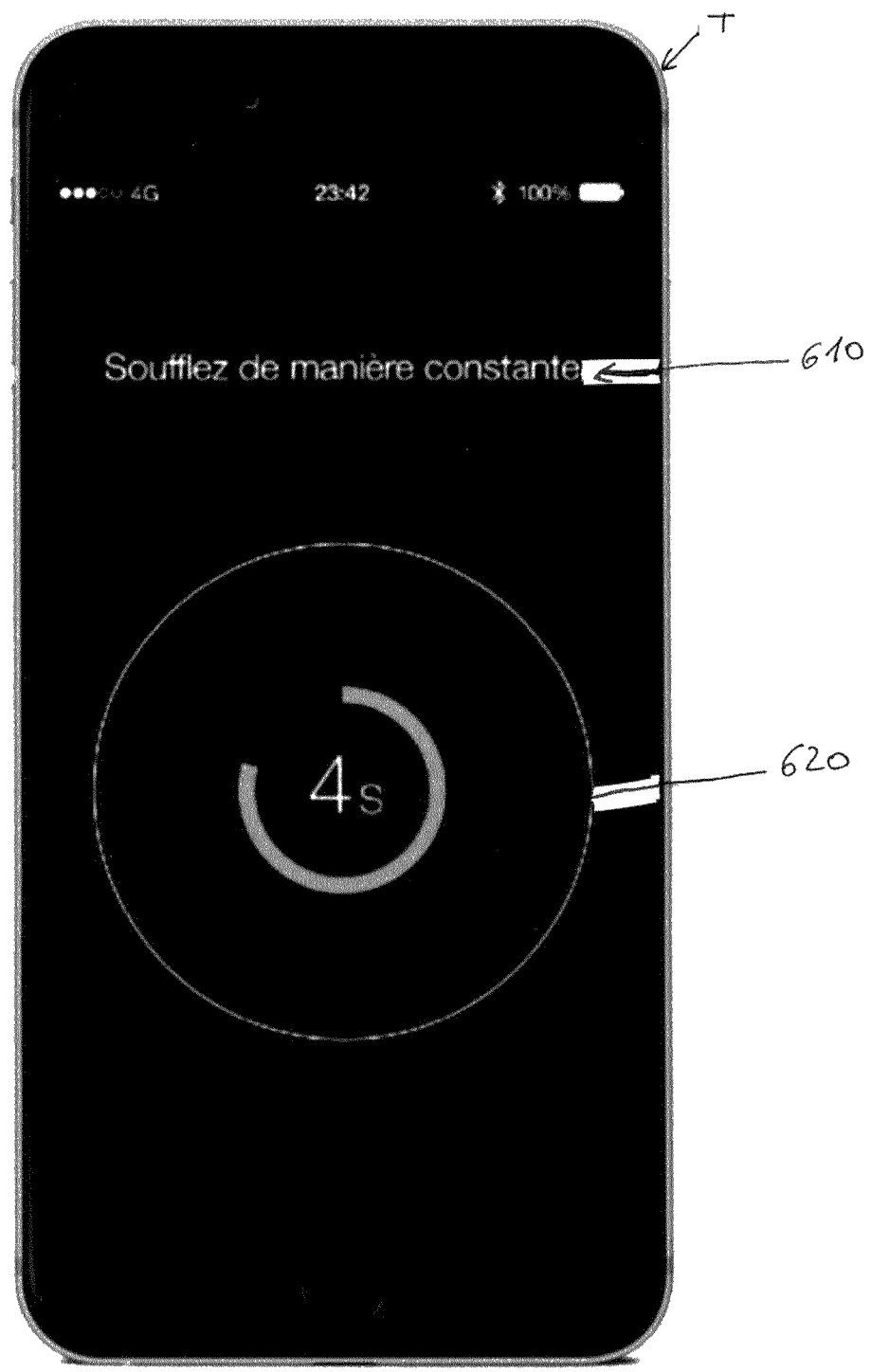
FIG. 19b shows a graphical interface that can be seen on a mobile terminal paired with a device according to the invention.

FIG. 19b: when the user presses button 12, terminal T displays instructions 610 for taking the measurement. This instruction 610, such as "blow evenly" or "a little less forcefully!," may vary throughout the breath to guide the user so that the exhaled air complies with what device A expects as an air sample in order for the measurement to be valid. A timer 620 is also displayed on the screen of terminal T to count down the amount of time the user needs to blow into mouthpiece 1. The countdown display is preferably in the form of a graphic, but can also be displayed as text (e.g. 4 seconds).

Figure 19C:
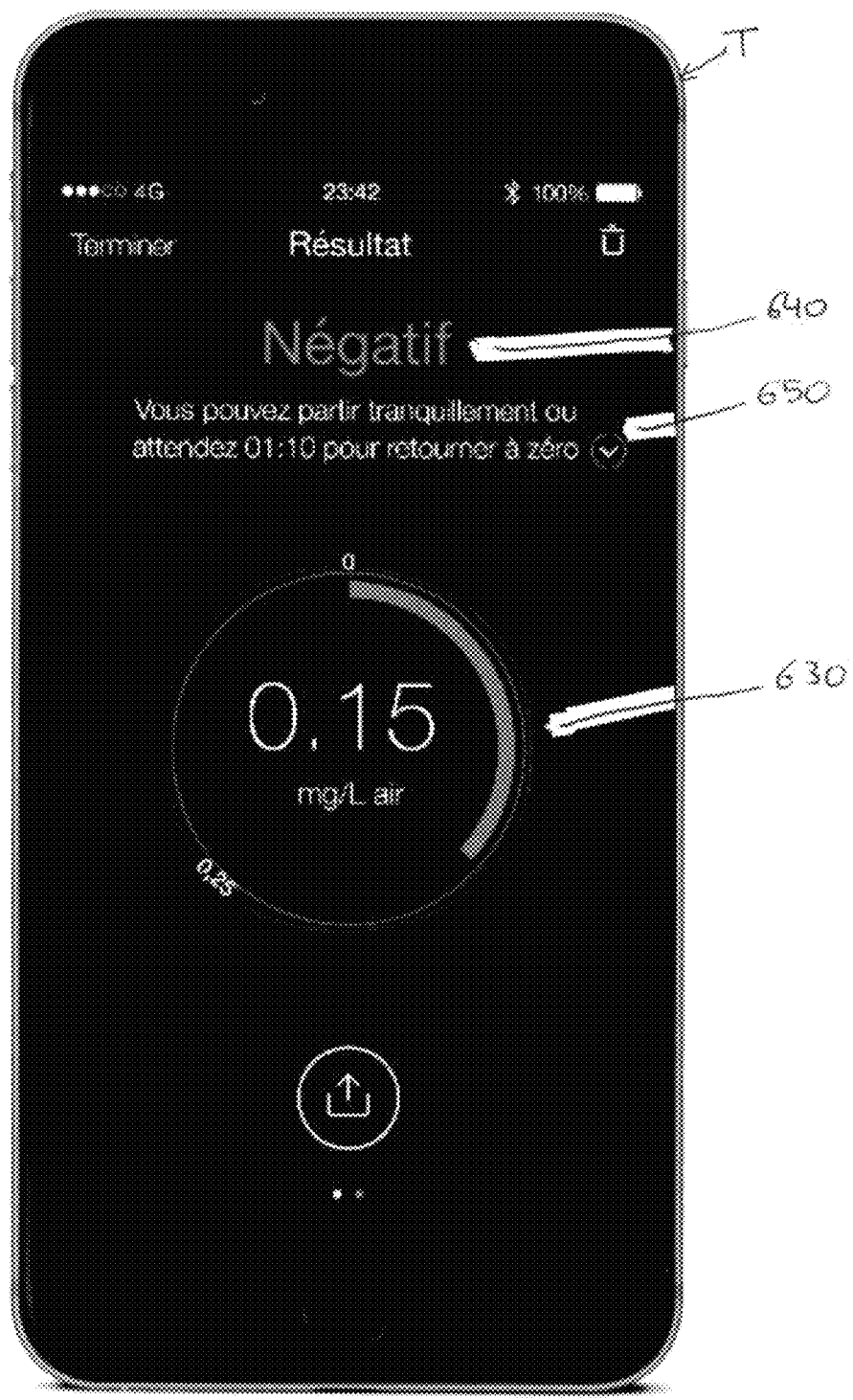
FIG. 19c shows a graphical interface that can be seen on a mobile terminal paired with a device according to the invention.

FIG. 19c: the mobile terminal displays measured concentration 630 measured by device A (e.g. blood alcohol). Terminal T can compare the value of this concentration to limit values. For example, in France the authorized limit for blood alcohol is 0.25 mg/$L_{air}$ (2018 data, excluding young drivers and passenger transport). Below that limit, a user can drive a ground-based motor vehicle (motorcycle, car). Beyond that limit, the user is not allowed to drive his/her vehicle and would incur sanctions in the event of non-compliance with this prohibition:

a fine and points taken away from his/her driver's license if the alcohol level is between 0.25 mg/$L_{air}$ and 0.40 mg/$L_{air}$.

a fine, suspension, or revocation of the driver's license, or even prison time, if the alcohol level is equal to or greater than 0.40 mg/$L_{air}$.

The limit values can be set on a menu of the application, not shown. They depend on the driver category (experienced, beginner, professional) and also the legislation of each country. If the user enables location services, then, if the user goes to another country, the computer application can offer to automatically update the limit values corresponding to his/her category in the new country.

In FIG. 19c, measured blood alcohol 630 is 0.15 mg/$L_{air}$. Since this concentration is less than the legal allowed limit, terminal T can display test result 640, for example "NEGATIVE" or "COMPLIANT>>. Terminal T can also display recommendations and/or other information 650. For example, the terminal can display a message telling the user he/she can drive (example: you may drive worry free" or that the last measurement is no longer valid. Terminal T can also calculate the time needed for the user's blood alcohol to drop to 0 mg/$L_{air}$ and display this time on terminal T in the form of a message (example: "estimated time to return to zero: 1 hour and 10 minutes") and/or a curve as shown in FIG. 19f. This time can be calculated as a function of previously-entered morphological data of the user (example: sex, age, height, weight) and/or depending on whether the user has consumed food or not while consuming alcohol. The blood alcohol drop-off times are longer if the person has an empty stomach and vice versa. Another possibility is to offer the user the ability to enter information on the circumstances of his/her consumption upon each measurement of a detected alcohol concentration (time when alcohol was consumed, type of beverage, time of last meal, etc.), with these data being recorded by the computer application. Using a learning method, the computer application could then predict with increasing accuracy the time needed for a given user's blood alcohol to return to 0 mg/$L_{air}$, as the number of the user's breaths grows.

Figure 19D:
FIG. 19d shows a graphical interface that can be seen on a mobile terminal paired with a device according to the invention.

FIG. 19d: here, measured blood alcohol 630 is equal to 0.32 mg/$L_{air}$. This concentration is between the limits of 0.25 mg/$L_{air}$ and 0.40 mg/$L_{air}$. Terminal T displays test result 640, for example: "POSITIVE" or "NON-COMPLIANT." Terminal T also displays recommendations and/or other information 650 appropriate for this case. For example, the terminal displays a message telling the user not to drive his/her vehicle (e.g. "you are over the legal limit" and/or "do not drive your vehicle"). Terminal T also displays the time needed for the user's blood alcohol to drop below the legal limit (e.g. "Estimated time to return to legal limit: 54 minutes"). This time is calculated as a function of previously-entered morphological data of the user and/or depending on whether the user has consumed food or not while consuming alcohol. The blood alcohol drop-off times are longer if the person has an empty stomach and vice versa. The computer application can also offer services to a user who is beyond the legal limit for driving. These services show up on terminal T as selectable icons 660 for contacting a taxi service, for instance.

Figure 19E:
FIG. 19e shows a graphical interface that can be seen on a mobile terminal paired with a device according to the invention.
Figure 19F:
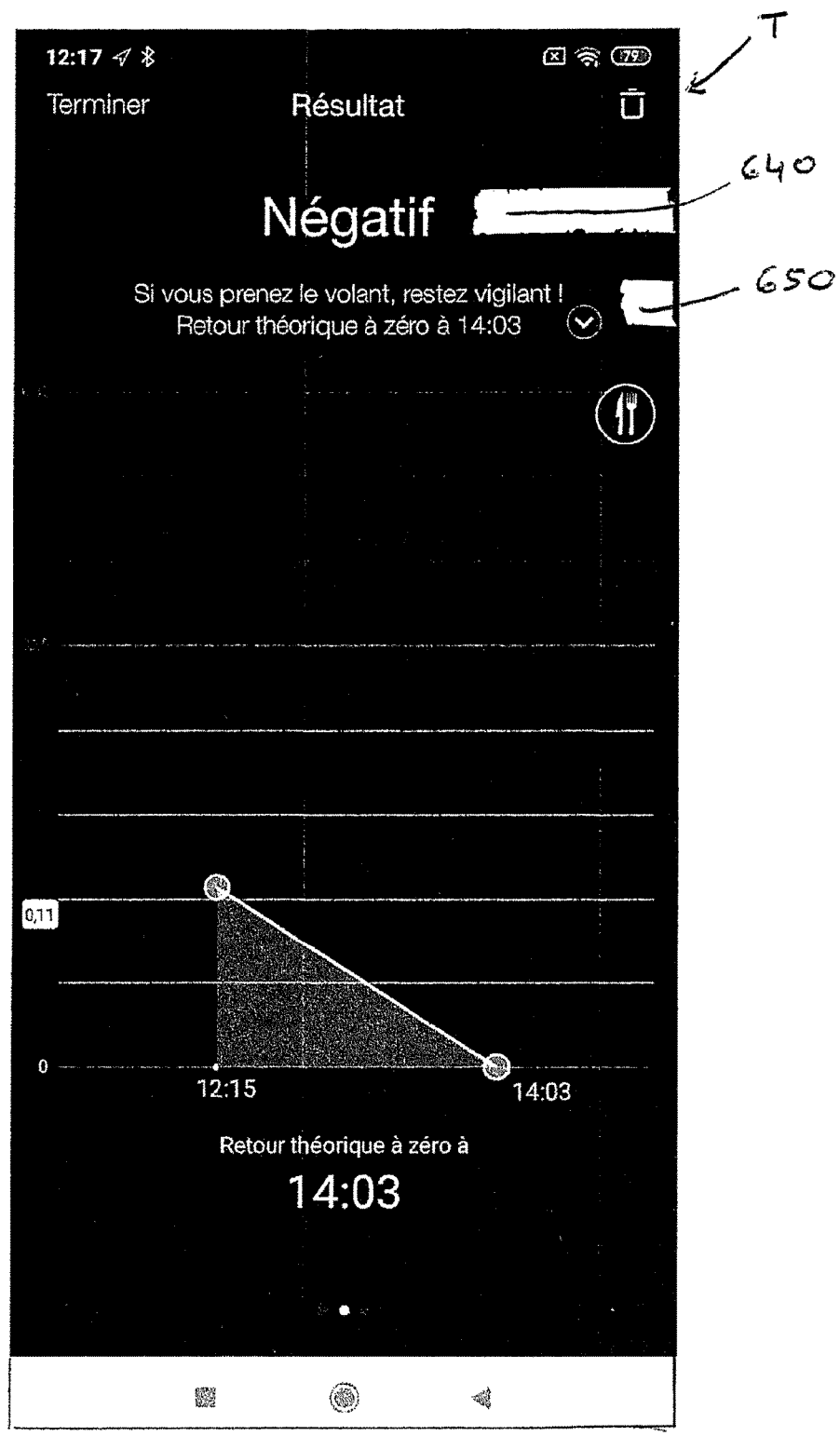
FIG. 19f shows a graphical interface that can be seen on a mobile terminal paired with a device according to the invention.

FIG. 19e: here, measured blood alcohol 630 is equal to 0.4 mg/$L_{air}$. This concentration places the user in a situation with the highest risk. Terminal T displays test result 640, for example: "CRIMINAL" and/or "DANGER." Terminal T also displays recommendations and/or other information 650 appropriate for this case. For example, the terminal displays a message strongly recommending that the user not drive his/her vehicle (e.g. "you are considerably over the legal limit" and/or "do not drive under any circumstances"). Terminal T also displays the time needed for the user's blood alcohol to drop below the legal limit (e.g. "Wait 1 hour 54 minutes before returning home"). This time is calculated as a function of previously-entered morphological data of the user and/or depending on whether the user has consumed food or not while consuming alcohol. The blood alcohol drop-off times are longer if the person has an empty stomach and vice versa.

In an embodiment variant, a means of identification of device A and a means of identification of the user are stored and linked in a database. Prior to measurement, the means of identification of device A and the means of identification of the user are acquired from the user's terminal T. The acquired means of identification of device A and the acquired means of identification of the user are analyzed. An instruction to take the measurement, generated from mobile terminal T, is sent to control unit 9 if and only if there is a match between the acquired means of identification of the device and the acquired means of identification of the user.

Figure 19G:
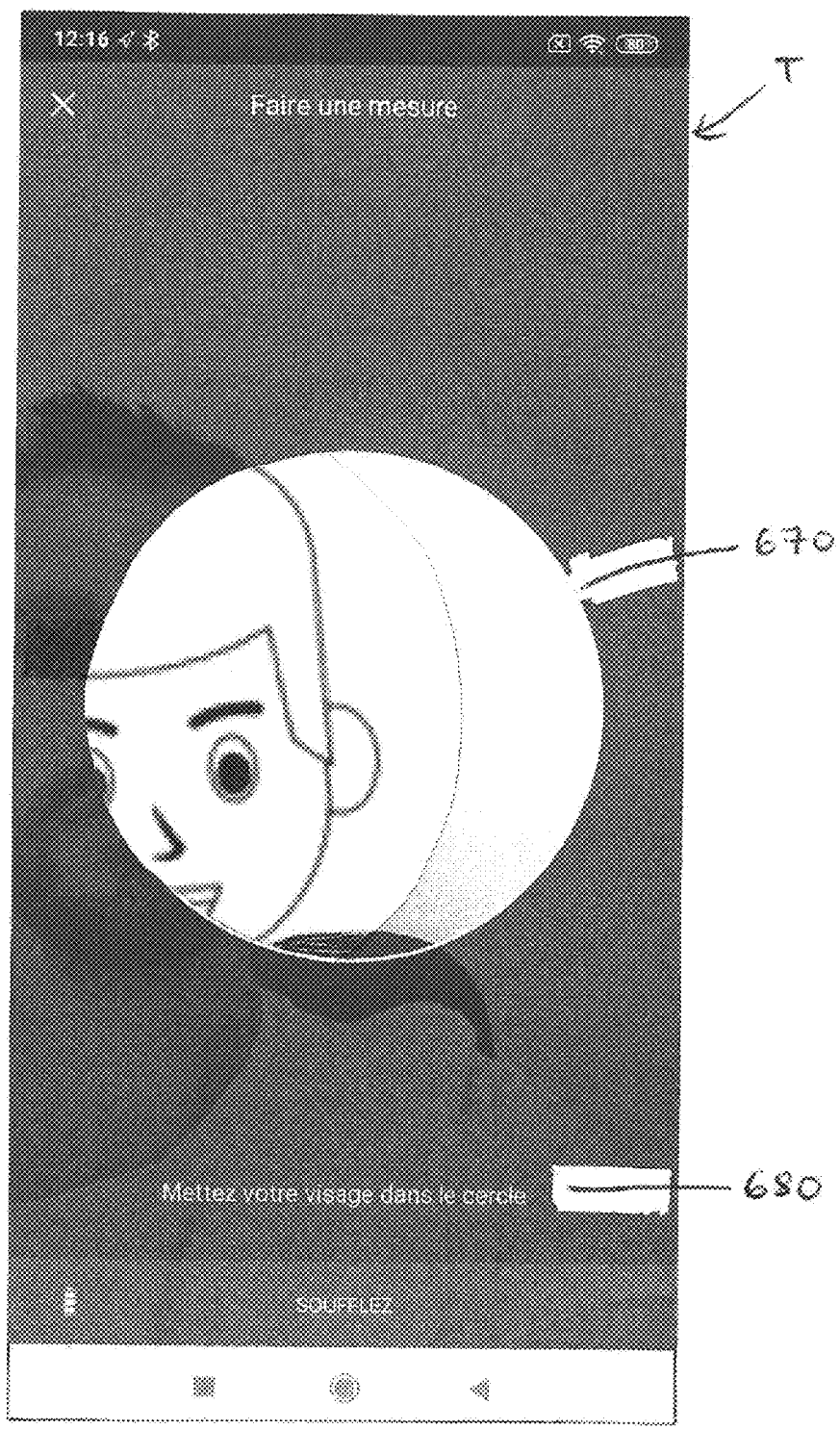
FIG. 19g shows a graphical interface that can be seen on a mobile terminal paired with a device according to the invention.
Figure 19H:
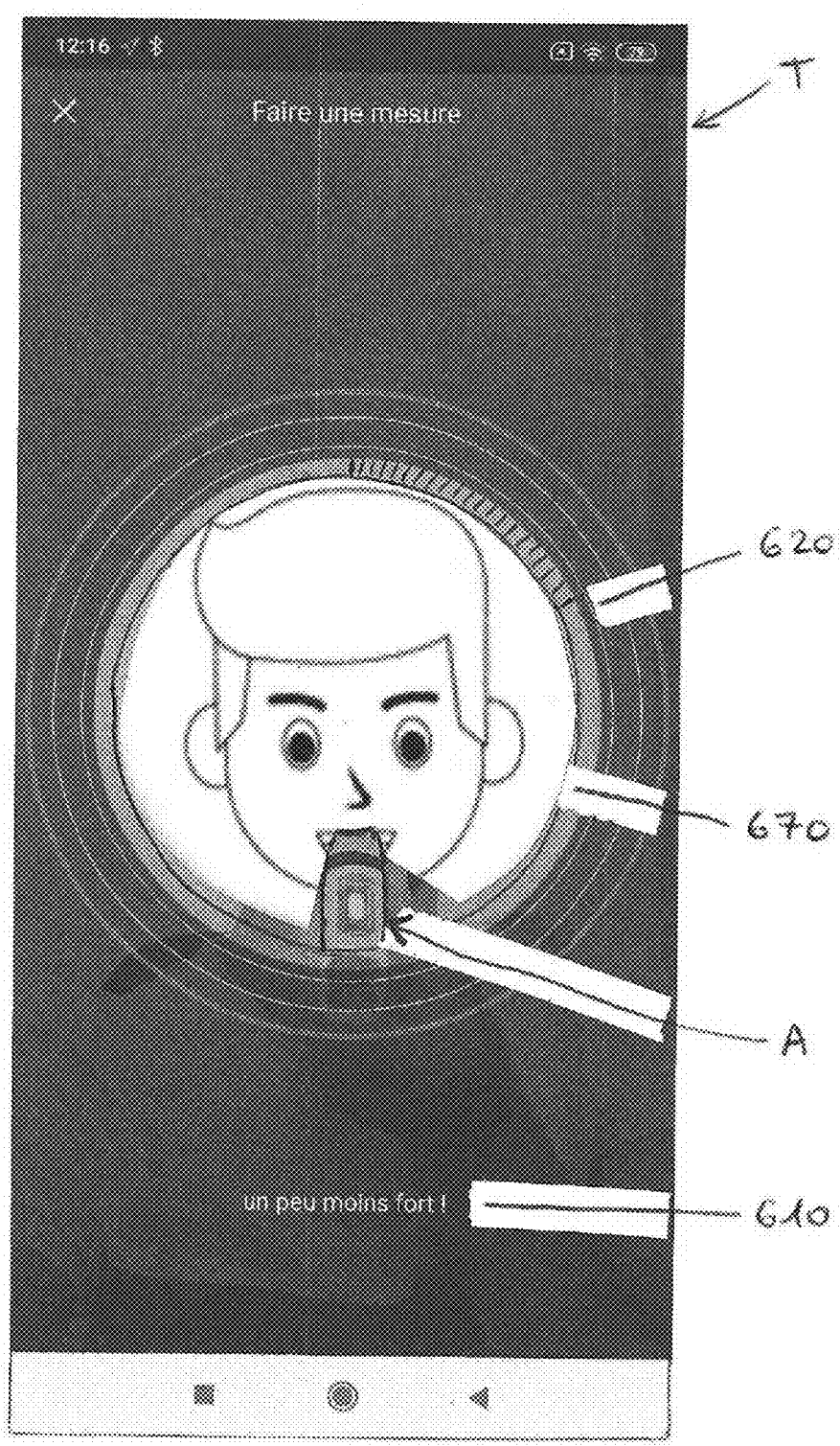
FIG. 19h shows a graphical interface that can be seen on a mobile terminal paired with a device according to the invention.
Figure 19I:
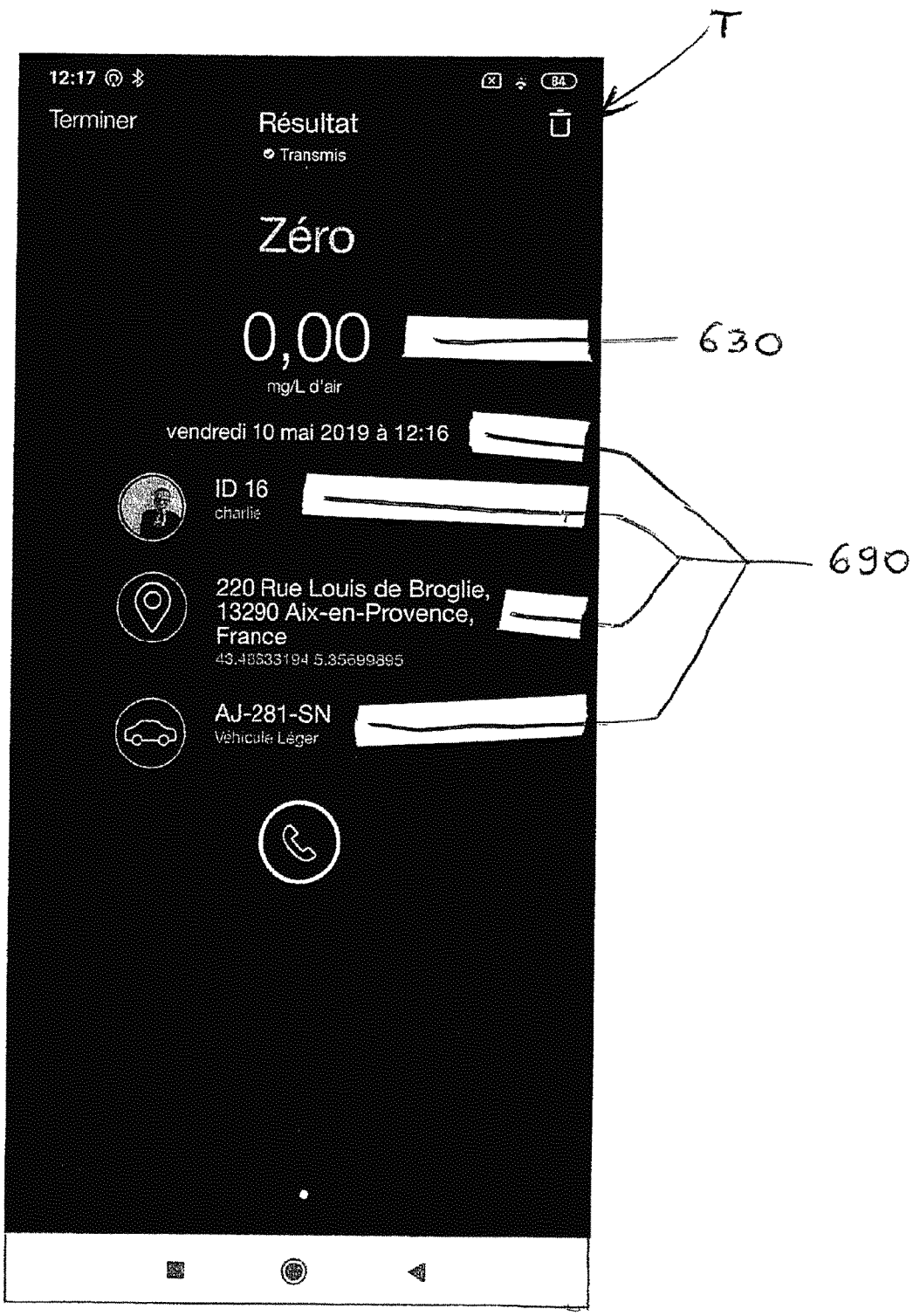
FIG. 19i shows a graphical interface that can be seen on a mobile terminal paired with a device according to the invention.

FIG. 19g: when the user presses button 600, the computer application displays on the screen of terminal T a recognition area 670 (shown here in the form of a circle) and suggestions 680 (such as, for example: "put your face in the circle") for adequate placement of the user's face and device A in said recognition area 670. Real-time acquisition of images of the user and device takes place via a camera of terminal T. These images are processed by an algorithm specific to the application, particularly a facial recognition algorithm. The image of the user's face as seen from the front, which in reality corresponds to a unique set of coordinates specific to the user's physiognomy, is first stored in a database during application configuration so that it can be compared and recognized during the user identification process. More specifically, these data are recorded in a personal account of the user on a secure server and the computer application can access these data when the user enters his/her account name and password. With regard to device A, the shape and possible markings thereof are also known to the application, and an algorithm for recognizing the shape and/or marking must make it possible to identify the device from different sides and from different angles so that the recognition thereof is independent of the way the user blows into said device.

Other means of identifying the user (for example, by fingerprint recognition or iris recognition) can also be considered. Likewise, device A can be identified by other means, for example by reading a QR-Code placed on said device.

FIG. 12i: Lastly, terminal T can also display a report containing the measured blood alcohol 630 and a collection of information 690 specific to the user (identifier, vehicle registration) and to the measurement (date and time, geolocation coordinates). The report can be stored in the user's personal account on a secure server, or sent directly to another person (for example, to a company manager in charge of monitoring sobriety of the company's employees, even if they are working remotely).

The use of breath testers as vehicle locking devices or as monitoring devices for companies with fleets of vehicles or dangerous machinery makes it possible to prevent vehicles from being driven or dangerous tools from being used by persons with a blood alcohol level exceeding legal limits or the internal rules of companies. But there are ways of circumventing the rules for users having exceeded the authorized limits, such as by using pump systems to inject air or having other sober persons blow into said breath testers.

The method of user identity verification proposed here aims to prevent such efforts to circumvent by ensuring the reliability of the blood alcohol measurements when the user is required to take such a measurement, but free not to personally blow into the verification device. It is advantageous in that it bypasses possible fraudulent uses of breath testers, which represents a danger for driving, while informing the user of the waiting time needed to drop below the authorized blood alcohol concentration limit.

The arrangement of the various elements and/or means and/or steps of the invention in the embodiments described above must not be construed as requiring such an arrangement in all implementations. In any event, it is understood that various modifications may be made to these elements and/or means and/or steps without exceeding the spirit and scope of the invention. In particular:

Device A does not necessarily have an elongated shape. It may still be compact in a configuration in which, for example, unitary assembly E and battery pack 7 are arranged side-by-side.

Enclosure 2 can be a single piece, that is, made of a single elongated tube with an inside wall defining the housing. It may also be made of more than two tubes 2A, 2B, for example three or four tubes fitting together.

Means of information 21 and/or on/off button 20 can be installed on tube 2A.

The measurement means can be suitable for processing signals other than infrared signals and/or for implementing an analysis technique other than photometry.

The sample can be forced to flow into chamber 3 by the partial vacuum created in said chamber by pumping means 8.

Outlet 80 of fan 8 can be configured so that the direction of breath fluid expulsion is normal to longitudinal axis X'-X' of chamber 3, or at an angle with respect to said axis. Opening 220B can then be positioned anywhere in the enclosure, for instance on a wall of tube 2A or tube 2B.

The features regarding common substrate 4a, measuring vessel 3, and temperature regulation described in reference to the first embodiment also apply to the second embodiment and the third embodiment.

In the appended figures, second chamber 110a, 110b, 110c is placed inside first chamber 101a, 101b, 101c. However, second chamber 110a, 110b, 110c can be in a position adjacent to first chamber 101a, 101b, 101c, the two chambers being in the same alignment or arranged side-by-side, for example.

Second chamber 110a, 110b, 110c does not necessarily have smaller dimensions than those of first chamber 101a, 101b, 101c. Indeed, it may have the same dimensions or larger dimensions. It is useful to clear the second chamber before taking a measurement so that the measurement will be as accurate as possible. Also, the larger the volume of second chamber 110a, 110b, 110c, the longer the clearing time thereof. It is therefore advantageous to have a second chamber of reduced dimensions so that it can be cleared as quickly as possible and a quick and accurate measurement can be obtained.

The invention claimed is:

1. A portable device for measuring the concentration of at least one component in a gas exhaled by a breath fluid, comprising:
a mouthpiece through which the breath fluid is exhaled, an enclosure incorporating:
a measuring vessel,
a measurement means for measuring the concentration of at least one component in a gas of the breath fluid flowing into the measuring vessel, an opening into which the mouthpiece) is installed,
a first chamber located upstream of the measuring vessel and comprising an inlet through which the exhaled breath fluid enters said first chamber, a second chamber located upstream of the measuring vessel, said second chamber comprising:
an inlet leading into the first chamber, an outlet in fluid communication with the measuring vessel and through which a portion of the exhaled breath fluid passes, and
an outlet leading to the ambient air, through which a portion of the exhaled breath fluid is expelled into the ambient air, wherein
the second chamber is placed inside the first chamber or in a position adjacent to said first chamber,
the outlet to the ambient air leads into the first chamber in such a way that only a portion of the exhaled breath fluid flowing into said first chamber enters the second chamber through the inlet of said second chamber, the other portion of the exhaled breath fluid being expelled into the ambient air,
the measuring vessel is made from a pliable, flexible substrate made in the shape of a tube, the pliable, flexible substrate comprises a first side and a second side, and said sides are opposite each other,
the first side is covered with a reflective metal material forming an optical reflection layer, and
the pliable, flexible substrate incorporates a resistive heating element and said heating element is in the form of a flexible electrical circuit into which are integrated one or more heating filaments in the form of strips of metal arranged on the second side.

2. The device according to claim 1, wherein the first chamber and the second chamber are made in the mouthpiece.

3. The device according to claim 1, wherein the first chamber and the second chamber are made in the enclosure.

4. The device according to claim 1, wherein:
the measuring vessel, the measurement means, a pumping means for extracting the breath fluid flowing into the measuring vessel, and the control unit are grouped together on a common substrate so as to form a grippable unitary assembly, said assembly being removably installed in the housing of the enclosure, and
the first chamber and the second chamber are made in the common substrate.

5. The device according to claim 1, wherein the second chamber has smaller dimensions than those of the first chamber.

6. The device according to claim 1, wherein the measuring vessel, the measurement means, a pumping means, and the control unit are grouped together on a common substrate so as to form a grippable unitary assembly, said assembly being removably installed in the housing of the enclosure.

7. The device according to claim 6, wherein:
the enclosure is made of at least two elongated tubes having a common longitudinal axis,
said tubes fitting together along said longitudinal axis in order to define the housing,
the unitary assembly is installed in one of the tubes, said tube forming a mouthpiece holder into which the mouthpiece is inserted.

8. The device according to claim 7, wherein the other tube forming the enclosure is suitable for receiving an electric battery pack for providing power to the grippable unitary assembly.

9. The device according to claim 6, wherein the common substrate is suitable for providing fluid communication between the measuring vessel and the outlet of the second chamber.

10. The device according to claim 6, wherein the common substrate comprises:
a housing in which the measuring vessel is installed,
at least one housing in which the measurement means is installed,
a housing in which the pumping means is installed, and
one or more features for receiving the control unit.

11. The device according to claim 6, wherein:
the common substrate comprises:
a first drill hole leading into a housing in which the measuring vessel is installed, so that said drill hole is in fluid communication with said chamber, and
a second drill hole leading into a chamber made in said substrate and in which a pressure sensor is installed, and
the outlet of the second chamber is in fluid communication with the first drill hole and with the second drill hole.

12. The device according to claim 11, wherein the first drill hole is conical and comprises a first hole and a second hole that leads into the housing in which the measuring vessel is installed, the diameter of said first hole being less than the diameter of said second hole.

13. The device according to claim 1, wherein said outlet to the ambient air is sized so that 80% to 98% of the breath fluid exhaled into the first chamber is expelled to the ambient air.

14. The device according to claim 1, wherein:
the inlet of the first chamber, the inlet of the second chamber, and the outlet of said second chamber are arranged in the same alignment,
the outlet to the ambient air is oriented in a direction perpendicular to this alignment.

15. The device according to claim 10, wherein the housing in which the pumping means is installed comprises a drill hole leading into the housing in which the measuring vessel is installed, so that said housings are in fluid communication.

16. The device according to claim 1, wherein:
the measuring vessel and the enclosure each have a longitudinal axis and these axes are parallel,
a pumping means is configured to expel the breath fluid flowing into the measuring vessel in a direction parallel to said longitudinal axes.

17. The device according to claim 1, wherein:
the measuring vessel is made from a pliable, flexible substrate made in the shape of a tube,
one side of the pliable, flexible substrate is covered with a reflective metal material forming an optical reflection layer,
the pliable, flexible substrate incorporates a resistive heating element, and
the pliable, flexible substrate comprises two opposing longitudinal edges that are secured to each other by bonding so as to maintain the shape of said substrate in the form of a tube, and
one of said edges has a strip free of any resistive heating element.

18. The device according to claim 1, wherein: the one or more heating filaments in the form of strips of metal having a thickness of 1 μm to 50 μm thick.

19. The device according to claim 18, wherein the heating filament or filaments cover the pliable, flexible substrate homogeneously in such a way that the density of electrical power generated by the resistive heating element is identical over the entire second side of said substrate.

20. The device according to claim 18, wherein the heating filament or filaments cover the pliable, flexible substrate non-homogeneously in such a way that the density of electrical power generated by the resistive heating element varies along a longitudinal axis and/or along a transverse axis of the pliable, flexible substrate.

21. The device according to claim 18, wherein the heating filaments form resistive heating sub-assemblies electrically connected in parallel.

22. The device according to claim 1, wherein:
the measuring vessel is in the form of a tube open at both ends,
the measurement means comprises:
an infrared radiation emitter installed at one end of measuring vessel so that an infrared radiation passes through said chamber, and
an infrared radiation detector installed at the other end of the measuring vessel, a cavity sealed against the breath fluid is placed between the infrared radiation emitter and the corresponding end of the measuring vessel, and a cavity sealed against the breath fluid is placed between the infrared radiation detector and the corresponding end of the measuring vessel.

23. The device according to claim 1, wherein said device is a breathalyzer or a breath tester.

24. A method for regulating the temperature of the measuring vessel of the device according to claim 18, comprising regulating the electrical energy injected into the resistive heating element thanks to a negative feedback loop based on: real-time measurement of the resistance of said element and the objective of achieving a resistance setting corresponding to a target heating temperature.

25. A method for using a device in accordance with claim 1, comprising:

recording and associating a means of identification of the device and a means of identification of a user in a database, prior to the measurement, acquiring the means of identification of the device and the means of identification of the user from a mobile terminal of the user, analyzing the acquired means of identification of the device and the acquired means of identification of the user, sending an instruction to the control unit to take the measurement only in the event of a match between the acquired means of identification of the device and the acquired means of identification of the user, said instruction being generated from the mobile terminal.

26. A method according to claim 25, wherein the acquisition of the user's means of identification is based on the implementation of an algorithm for facial recognition of said user.

27. The method according to claim 25, wherein the acquisition of the means of identification of the device is based on the implementation of an algorithm for recognizing the shape of said device.

28. The method according to claim 25, wherein the acquisition of the means of identification of the device is based on the implementation of an algorithm for recognizing a marking placed on said device.

* * * * *